United States Patent
Pollner et al.

(10) Patent No.: US 11,035,012 B2
(45) Date of Patent: *Jun. 15, 2021

(54) CAPTURE PROBES IMMOBILIZABLE VIA L-NUCLEOTIDE TAIL

(71) Applicant: GEN-PROBE INCORPORATED, San Diego, CA (US)

(72) Inventors: Reinhold Pollner, San Diego, CA (US); Mehrdad Majlessi, Escondido, CA (US); Susan Yamagata, San Diego, CA (US); Michael M. Becker, San Diego, CA (US); Mark Reynolds, Carlsbad, CA (US); Lyle Arnold, Poway, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 398 days.

This patent is subject to a terminal disclaimer.

(21) Appl. No.: 15/904,232

(22) Filed: Feb. 23, 2018

(65) Prior Publication Data

US 2018/0251862 A1 Sep. 6, 2018

Related U.S. Application Data

(63) Continuation of application No. 13/823,551, filed as application No. PCT/US2011/052050 on Sep. 16, 2011, now Pat. No. 9,938,590.

(60) Provisional application No. 61/383,728, filed on Sep. 16, 2010.

(51) Int. Cl.
*C12Q 1/68* (2018.01)
*C07H 21/00* (2006.01)
*C12Q 1/70* (2006.01)
*C12Q 1/6837* (2018.01)

(52) U.S. Cl.
CPC ........... *C12Q 1/707* (2013.01); *C12Q 1/6837* (2013.01); *C12Q 1/703* (2013.01); *Y02A 50/30* (2018.01)

(58) Field of Classification Search
CPC .......... C12Q 1/00; C12Q 1/68; C12Q 1/6832; C07H 21/00
See application file for complete search history.

(56) References Cited

U.S. PATENT DOCUMENTS

| | | | |
|---|---|---|---|
| 4,988,617 A | 1/1991 | Landegren et al. | |
| 5,043,272 A * | 8/1991 | Hartley | C12Q 1/6844 435/5 |
| 5,374,395 A | 12/1994 | Robinson et al. | |
| 5,484,909 A * | 1/1996 | Nietupski | C07H 21/00 435/252.9 |
| 5,521,301 A * | 5/1996 | Wallace | C12Q 1/6881 435/6.11 |
| 5,582,988 A | 12/1996 | Backus et al. | |
| 5,670,325 A | 9/1997 | Lapidus et al. | |
| 5,759,773 A | 6/1998 | Tyagi et al. | |
| 5,952,178 A | 9/1999 | Lapidus et al. | |
| 5,994,058 A * | 11/1999 | Senapathy | C12Q 1/6853 435/6.1 |
| 6,110,678 A | 8/2000 | Weisburg et al. | |
| 6,194,149 B1 | 2/2001 | Neri et al. | |
| 6,251,666 B1 | 6/2001 | Beigelman | |
| 9,051,601 B2 * | 6/2015 | Becker | C12N 15/11 |
| 9,225,293 B2 * | 12/2015 | Teggatz | H03F 1/305 |
| 9,938,590 B2 * | 4/2018 | Pollner | C12Q 1/6837 |
| 2001/0053519 A1 * | 12/2001 | Fodor | B01J 19/0046 435/6.11 |
| 2002/0119442 A1 * | 8/2002 | Dunlop | C12Q 1/6844 435/5 |
| 2002/0119458 A1 | 8/2002 | Suyama et al. | |
| 2002/0164659 A1 | 11/2002 | Rao et al. | |
| 2002/0172950 A1 | 11/2002 | Daryn et al. | |
| 2003/0069701 A1 | 4/2003 | Toshiko et al. | |
| 2003/0087230 A1 | 5/2003 | Wengel | |
| 2003/0194723 A1 | 10/2003 | Cunningham et al. | |
| 2005/0089860 A1 | 4/2005 | Arita | |
| 2005/0164226 A1 | 7/2005 | Huang | |

(Continued)

FOREIGN PATENT DOCUMENTS

| | | |
|---|---|---|
| WO | 03/039523 A2 | 5/2003 |
| WO | WO 2013/037531 A1 | 3/2012 |

OTHER PUBLICATIONS

Bau et al.Targeted next-generation sequencing by specific capture of multiple genomic loci using low-volume microfluidic DNA arrays. Anal. Bioanal. Chem. 393 :171 -175 (Year: 2009).*

(Continued)

*Primary Examiner* — Ethan C Whisenant
(74) *Attorney, Agent, or Firm* — Alston & Bird LLP; Jeff Landes

(57) ABSTRACT

The invention provides chimeric capture probes immobilizable via an L-nucleic acid tail that can bind to a complementary L-nucleic acid in an immobilized probe. The capture probes are useful for capturing a target nucleic acid from a sample. The L-nucleic acid in the tail of the capture probe bind to the complementary L-nucleic acid in the immobilized probe with similar affinity as would otherwise equivalent D-nucleic acids. However, the L-nucleic acid of the capture probe tail and immobilized probes do not form stable duplexes with D-nucleic acids present in the in the sample containing the target nucleic acid. Binding of nucleic acids in the sample directly to immobilized probe or to the tail of the capture probe is reduced or eliminated increasing the sensitivity and/or specificity of the assay.

19 Claims, 2 Drawing Sheets
Specification includes a Sequence Listing.

(56) References Cited

U.S. PATENT DOCUMENTS

| | | | |
|---|---|---|---|
| 2006/0063264 A1* | 3/2006 | Turner | B01L 3/5085 436/8 |
| 2006/0210967 A1 | 9/2006 | Agan et al. | |
| 2006/0292438 A1* | 12/2006 | Greenfield | B82Y 10/00 429/63 |
| 2007/0003936 A1 | 1/2007 | Gite et al. | |
| 2007/0269344 A1 | 11/2007 | Ohnishi et al. | |
| 2008/0125324 A1* | 5/2008 | Petersdorf | C12Q 1/6813 506/1 |
| 2008/0200347 A1 | 8/2008 | Yoshida et al. | |
| 2008/0286775 A1* | 11/2008 | Becker | C12N 15/1006 435/6.11 |
| 2009/0105081 A1* | 4/2009 | Rodesch | C12Q 1/6813 506/1 |
| 2009/0203540 A1* | 8/2009 | Middle | C12Q 1/6813 506/9 |
| 2009/0221438 A1* | 9/2009 | Kitzman | C12N 15/1093 506/9 |
| 2010/0029498 A1* | 2/2010 | Gnirke | C12Q 1/6869 506/9 |
| 2010/0121056 A1* | 5/2010 | Christensen | C07H 21/02 544/251 |
| 2011/0250599 A1 | 10/2011 | Becker et al. | |
| 2012/0196765 A1 | 8/2012 | Kawase et al. | |

OTHER PUBLICATIONS

Dahl et al., Multigene amplification and massively parallel sequencing for cancer mutation discovery. PNAS 104(22) : 9387-9392 (Year: 2007).*
Eid et al.Real-Time DNA Sequencing from Single Polymerase Molecules. Science 323:133 (Year: 2009).*
Gnirke et al., Solution hybrid selection with ultra-long oligonucleotides for massively parallel targeted sequencing. Nature Biotechnology 27(2) :182 (Year: 2009).*
Harris et al., Single-Molecule DNA Sequencing of a Viral Genome. Science 320 : 106 (Year: 2008).*
Hauser et al., Utilising the left-helical conformation of L-DNA for analysing different marker types on a single universal microarray platform. Nucleic Acids Research 34(18) : 5101-5111 (Year: 2006).*
Ng et al., Targeted capture and massively parallel sequencing of 12 human exomes. Nature 461 : 272 (Year: 2009).*
Summerer et al., Microarray-based multicycle-enrichment of genomic subsets for targeted next-generation sequencing. Genome Research 19 :1616-1621 (Year: 2009).*
Summerer, D. Enabling technologies of genomic-scale sequence enrichment for targeted high-throughput sequencing. Genomics 94:363 (Year: 2009).*
APO Patent Examination Report No. 1, Australian Patent Application No. 2011301804, dated Mar. 25, 2014.
APO Patent Examination Report No. 2, Australian Patent Application No. 2011301804, dated May 21, 2015.
APO Notice of Acceptance, Australian Patent Application No. 2011301804, dated Jul. 2, 2015.
CIPO Examination Report, Canadian Application No. 2,811,333, dated Jul. 7, 2017.
EPO Communication pursuant to Article 94(3) EPC, European Application No. 11764910.3, dated Jan. 7, 2015.
EPO Communication pursuant to Article 94(3) EPC, European Application No. 11764910.3, dated Feb. 16, 2016.
EPO Extended European Search Report, European Application No. 17199730.7, dated Mar. 12, 2018.
PCT Written Opinion, International Application No. PCT/US2011/052050, dated Feb. 16, 2012.
PCT International Search Report, International Application No. PCT/US2011/052050, dated Feb. 16, 2012.
PCT International Preliminary Report on Patentability, International Application No. PCT/US2011/052050, dated Mar. 19, 2013.
USPTO Non-Final Rejection, U.S. Appl. No. 13/823,551, dated May 7, 2015.
USPTO Final Rejection, U.S. Appl. No. 13/823,551, dated Aug. 25, 2015.
USPTO Final Rejection, U.S. Appl. No. 13/823,551, dated Jan. 4, 2016.
USPTO Final Rejection, U.S. Appl. No. 13/823,551, dated Aug. 16, 2016.
USPTO Notice of Allowance, U.S. Appl. No. 13/823,551, dated Nov. 24, 2017.
Archer et al, "Magnetic bead-based solid phase for selective extraction of genomic DNA," Analytical Biochemistry, 2006, vol. 355, No. 2, p. 285-297.
Cheng et al., "Nanotechnologies for biomolecular detection and medical diagnostics," Current Opinion in Chemical Biology, 2006, vol. 10, p. 11-19.
Hauser et al., "Utilising the left-helical conformation of L-DNA for analysing different marker types on a single universal microarray platform," Nucleic Acids Research, 2006, vol. 34, No. 18, p. 5101-5111.
Hayashi et al., "Application of L-DNA as a molecular tag," Nucleic Acids Symposium Series, 2005, No. 49, p. 261-262.
Hayashi et al., "Detection of L-DNA-Tagged PCR Products by Surface Plasmon Resonance Imaging," ChemBioChem, 2007, vol. 8, p. 169-171.
Hayashi et al., "Genotyping by allele-specific L-DNA-tagged PCR," Journal of Biotechnology 135, 2008, p. 157-160.
Sato et al., "Rapid Aggregation of Gold Nanoparticles Induced by Non-Cross-Linking DNA Hybridization," J. Am. Chem. Soc., vol. 125, p. 8102-8103.
Urdea et al., "A comparison of non-radioisotopic hybridization assay methods using fluorescent, chemiluminescent and enzyme labeled synthetic oligodeoxyribonucleotide probes," Nucleic Acids Research, 1988, vol. 16, No. 11, p. 4937-4966.
CIPO Examination Report, Canadian Application No. 2,811,333, dated Aug. 20, 2018.
U.S. Appl. No. 61/383,728, filed Sep. 16, 2010, Expired.
U.S. Appl. No. 13/823,551, filed Jun. 7, 2013, U.S. Pat. No. 9,938,590 B2, Issued.
PCT/US2011/052050, filed Sep. 16, 2011, WO 2012/037531, Expired.

* cited by examiner

SEQUENCE LISTING

```
<160> NUMBER OF SEQ ID NOS: 30

<210> SEQ ID NO 1
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(40)
<223> OTHER INFORMATION: /note="This sequence may encompass 1 to 40
      nucleotides"

<400> SEQUENCE: 1
aaaaaaaaaa aaaaaaaaaa aaaaaaaaaa aaaaaaaaaa                               40

<210> SEQ ID NO 2
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
tttttttttt tttt                                                          14

<210> SEQ ID NO 3
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
aaaaaaaaaa aaaaaaaaaa aaaaaaaaaa                                         30

<210> SEQ ID NO 4
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 4
cucuuccaau cguccgcgug cuuauuuaaa aaaaaaaaaa aaaaaaaaaa aaaaaa            57
```

```
<210> SEQ ID NO 5
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
<220> FEATURE:
<221> NAME/KEY: source
<223> OTHER INFORMATION: /note="Description of Combined DNA/RNA
      Molecule: Synthetic probe"

<400> SEQUENCE: 5
cuccuaucgu uccauaguca ccct                                            24

<210> SEQ ID NO 6
<211> LENGTH: 4881
<212> TYPE: DNA
<213> ORGANISM: Unknown
<220> FEATURE:
<221> NAME/KEY: source
<223> OTHER INFORMATION: /note="Description of Unknown: Target
      ribosomal polynucleotide"

<400> SEQUENCE: 6 tttttctga gaatttgatc ttggttcaga ttgaacgctg gcggcgtgga tgaggcatgc        60
aagtcgaacg gagcaattgt ttcggcaatt gtttagtggc ggaagggtta gtaatgcata      120
gataatttgt ccttaacttg ggaataacgg ttggaaacgg ccgctaatac cgaatgtggc      180
gatatttggg catccgagta acgttaaaga aggggatctt aggacctttc ggttaaggga      240
gagtctatgt gatatcagct agttggtggg gtaaaggcct accaaggcta tgacgtctag      300
gcggattgag agattggccg ccaacactgg gactgagaca ctgcccagac tcctacggga      360
ggctgcagtc gagaatcttt cgcaatggac ggaagtctga cgaagcgacg ccgcgtgtgt      420
gatgaaggct ctagggttgt aaagcacttt cgcttgggaa taagagaagg cggttaatac      480
ccgctggatt tgagcgtacc aggtaaagaa gcaccggcta actccgtgcc agcagctgcg      540
gtaatacgga gggtgctagc gttaatcgga tttattgggc gtaaagggcg tgtaggcgga      600
aaggtaagtt agttgtcaaa gatcgggggct caaccccgag tcggcatcta atactatttt      660
tctagagggt agatggagaa agggaatttc acgtgtagc ggtgaaatgc gtagatatgt      720
ggaagaacac cagtggcgaa ggcgcttttc taatttatac ctgacgctaa ggcgcgaaag      780
caaggggagc aaacaggatt agatacctg gtagtccttg ccgtaaacga tgcatacttg      840
atgtggatgt tctcaacccc atccgtgtcg gagctaacgc gttaagtatg ccgcctgagg      900
agtacactcg caagggtgaa actcaaaaga attgacgggg gcccgcacaa gcagtggagc      960
atgtggttta attcgatgca acgcgaagga ccttacctgg gtttgacatg tatatgaccg     1020
cggcagaaat gtcgttttcc gcaaggacat atacacaggt gctgcatggc tgtcgtcagc     1080
tcgtgccgtg aggtgttggg ttaagtcccg caacagcgc aacccttatc gttagttgcc     1140
agcacttagg gtgggaactc taacgagact gcctggtta accaggagga aggcgaggat     1200
gacgtcaagt cagcatggcc cttatgccca gggcgacaca cgtgctacaa tggccagtac     1260
agaaggtagc aagatcgtga gatggagcaa atcctcaaag ctggcccag ttcggattgt     1320 agtctgcaac tcgactacat gaagtcggaa ttgctagtaa tggcgtgtca gccataacgc     1380
cgtgaatacg ttcccgggcc ttgtacacac cgcccgtcac atcatgggag ttggttttac     1440
cttaagtcgt tgactcaacc cgcaagggag agaggcgccc aagtgaggc tgatgactag     1500
```

-continued

```
gatgaagtcg taacaaggta gccctaccgg aaggtggggc tggatcacct ccttttaagg    1560
ataaggaaga agcctgagaa ggtttctgac taggttgggc aagcatttat atgtaagagc    1620
aagcattcta tttcatttgt gttgttaaga gtagcgtggt gaggacgaga catatagttt    1680
gtgatcaagt atgttattgt aaagaaataa tcatggtaac aagtatattt cacgcataat    1740
aatagacgtt taagagtatt tgtcttttag gtgaagtgct tgcatggatc tatagaaatt    1800
acagaccaag ttaataagag ctattggtgg atgccttggc attgacaggc gaagaaggac    1860
gcgaatacct gcgaaaagct ccggcgagct ggtgataagc aaagacccgg aggtatccga    1920
atggggaaac ccggtagagt aatagactac cattgcatgc tgaatacata ggtatgcaga    1980
gcgacacctg ccgaactgaa acatcttagt aggcagagga aaagaaatcg aagagattcc    2040
ctgtgtagcg gcgagcgaaa ggggaatagc ctaaaccgag ctgataaggc tcggggttgt    2100
aggattgagg ataaaggatc aggactccta gttgaacaca tctggaaaga tggatgatac    2160
agggtgatag tcccgtagac gaaaggagag aaagaccgac ctcaacacct gagtaggact    2220
agacacgtga aacctagtct gaatctgggg agaccactct ccaaggctaa atactagtca    2280
atgaccgata gtgaaccagt actgtgaagg aaaggcgaaa agaacccttg ttaagggagt    2340
gaaatagaac ctgaaaccag tagcttacaa gcggtcggag accaatggcc cgtaagggtc    2400
aaggttgacg gcgtgccttt tgcatgatga gccaggagt taagctaaac ggcgaggtta    2460
agggatatac attccggagc cggagcgaaa gcgagtttta aaagagcgaa gagtcgtttg    2520
gtttagacac gaaaccaagt gagctatttta tgaccaggtt gaagcatggg taaaactatg    2580
tggaggaccg aactagtacc tgttgaaaaa ggtttggatg agttgtgaat aggggtgaaa    2640
ggccaatcaa acttggagat atcttgttct ctccgaaata actttagggt tagcctcgga    2700
taatgagctt tggggggtag agcactgaat tctagcgggg gcctaccggc ttaccaacgg    2760
aaatcaaact ccgaatacca gaagcgagtc cgggagatag acagcggggg ctaagcttcg    2820
ttgtcgagag gggaacagcc cagaccgccg attaaggtcc ctaattttat gctaagtggg    2880
taaggaagtg atgattcgaa gacagttgga atgttggctt agaggcagca atcatttaaa    2940
gagtgcgtaa cagctcacca atcgagaatc attgcgccga taataaacgg gactaagcat    3000
aaaaccgaca tcgcgggtgt gtcgataaga cacgcggtag gagagcgtag tattcagcag    3060
agaaggtgta ccggaaggag ggctggagcg gatactagtg aagatccatg gcataagtaa    3120
cgataaaggg agtgaaaatc tccctcgccg taagcccaag gtttccaggg tcaagctcgt    3180
cttccctggg ttagtcggcc cctaagttga ggcgtaactg cgtagacgat ggagcagcag    3240
gttaaatatt cctgcaccac ctaaaactat agcgaaggaa tgacggagta agttaagcac    3300
gcggacgatt ggaagagtcc gtagagcgat gagaacggtt agtaggcaaa tccgctaaca    3360
taagatcagg tcgcgatcaa ggggaatctt cggaggaacc gatggtgtgg agcgaggctt    3420
tcaagaaata atttctagct gttgatggtg accgtaccaa aaccgacaca ggtgggcgag    3480
atgaatattc taaggcgcgc gagataactt tcgttaagga actcggcaaa ttatccccgt    3540
aacttcggaa taaggggagc ctttaggggt gactatggaa cgataggagc cccgggggc    3600
cgcagagaaa tggcccaggc gactgtttag caaaaacaca gcactatgca aacctctaag    3660
gggaagtata tggtgtgacg cctgcccaat gccaaaaggt taagggata tgtcagctgt    3720
aaagcgaagc attgaaccta gcccctggta aatggccgcc gtaactataa cggtgctaag    3780
gtagcgaaat tccttgtcgg gtaagttccg acctgcacga atggtgtaac gatctgggca    3840
ctgtctcaac gaaagactcg gtgaaattgt agtagcagtg aagatgctgt ttacccgcga    3900
```

```
aaggacgaaa agaccccgtg aacctttact gtactttggt attggttttt ggtttgttat    3960
gtgtaggata gccaggagac taagaacact cttcttcagg agagtgggag tcaacgttga    4020
aatactggtc ttaacaagct gggaatctaa cattattcca tgaatctgga agatggacat    4080
tgccagacgg gcagttttac tggggcggta tcctcctaaa aagtaacgga ggagcccaaa    4140
gcttatttca tcgtggttgg caatcacgag tagagcgtaa aggtataaga taggttgact    4200
gcaagaccaa caagtcgagc agagacgaaa gtcgggctta tgatccggc ggtggaaagt     4260 ggaatcgccg tcgcttaacg gataaaaggt actccgggga taacaggctg atcgccacca    4320
agagttcata tcgacgtggc ggtttggcac ctcgatgtcg gctcatcgca tcctgggct     4380 ggagaaggtc ccaagggttt ggctgttcgc caattaaagc ggtacgcgag ctgggttcaa    4440
aacgtcgtga gacagtttgg tctctatcct tcgtgggcgc aggatacttg agaggagctg    4500
ttcctagtac gagaggaccg gaatggacga accaatggtg tatcggttgt tttgccaaga    4560
gcatagccga gtagctacgt tcggaaagga taagcattga aagcatctaa atgccaagcc    4620
tccctcaaga taaggtatcc caatgagact ccatgtagac tacgtggttg ataggttgga    4680
ggtgtaagca cagtaatgtg ttcagctaac caatactaat aagtccaaag acttggtctt    4740
tttatgattg gaagagccga aaggcaaaga caataagaaa aagagtagag agtgcaagtg    4800
cgtagaagac aagcttttaa gcgtctatta gtatacgtga gaaacgatac caggattagc    4860
ttggtgataa tagagagagg a                                              4881

<210> SEQ ID NO 7
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 7
uuuaagcagu ggguucccut taaaaaaaa aaaaaaaaa aaaaaaaaaa aa               52

<210> SEQ ID NO 8
<211> LENGTH: 62
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 8
gcagcugcuu auaugcagca aucugagggt ttaaaaaaaa aaaaaaaaa aaaaaaaaaa      60 aa                                                                   62

<210> SEQ ID NO 9
<211> LENGTH: 56
<212> TYPE: DNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 9
acuagcuuga agcaccaucc aaatttaaaa aaaaaaaaa aaaaaaaaaa aaaaaa        56

<210> SEQ ID NO 10
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 10 uccaguccccc ccuuuucuuu uaaatttaaa aaaaaaaaaa aaaaaaaaaa aaaaaaa      57

<210> SEQ ID NO 11
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 11
guagcugaag aggcacaggc uccgtttaaa aaaaaaaaaa aaaaaaaaaa aaaaaaa       57

<210> SEQ ID NO 12
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 12
aagccuccua cuaucauuau tttaaaaaaa aaaaaaaaaa aaaaaaaaaa aaa           53

<210> SEQ ID NO 13
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

-continued

<400> SEQUENCE: 13
uuuauauuua uauaauucac uucuccaauu gucctuuaaa aaaaaaaaaa aaaaaaaaaa    60
aaaaaaa    67

<210> SEQ ID NO 14
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 14 ggagggcau acauugcutt taaaaaaaaa aaaaaaaaaa aaaaaaaaaa a    51

<210> SEQ ID NO 15
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 15
ugagguauua caauuuauua atttaaaaaa aaaaaaaaaa aaaaaaaaaa aaaa    54

<210> SEQ ID NO 16
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 16
uucuuguggg uuggggucug uggguacaca gutuaaaaaa aaaaaaaaaa aaaaaaaaaa    60
aaaa    64

<210> SEQ ID NO 17
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 17

```
gccacugucu ucugcucuuu ctttaaaaaa aaaaaaaaaa aaaaaaaaaa aaaa          54
```

<210> SEQ ID NO 18
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 18

```
gucuccgcuu cuuccugcca uaggatttaa aaaaaaaaaa aaaaaaaaaa aaaaaaaa      58
```

<210> SEQ ID NO 19
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 19

```
ggucuucugg ggcuuguucc aucuaucttt aaaaaaaaaa aaaaaaaaaa aaaaaaaaaa    60
```

<210> SEQ ID NO 20
<211> LENGTH: 62
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 20

```
ucuuguauua cuacugcccc uucaccuuut taaaaaaaaa aaaaaaaaaa aaaaaaaaaa    60
aa                                                                  62
```

<210> SEQ ID NO 21
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 21

```
ccaucuuccc ccugcuaauu uuatttaaaa aaaaaaaaaa aaaaaaaaaa aaaaaa        56
```

<210> SEQ ID NO 22
<211> LENGTH: 65

```
-continued

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 22
acuaauuuau cuacuuguuc auuccucca autttaaaaa aaaaaaaaaa aaaaaaaaaa    60
aaaaa                                                               65

<210> SEQ ID NO 23
<211> LENGTH: 62
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 23
gcuauuaagu cuuuugaugg gucauaauat ttaaaaaaaa aaaaaaaaaa aaaaaaaaaa    60
aa                                                                  62

<210> SEQ ID NO 24
<211> LENGTH: 68
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 24
uggaauauug cuggugaucc uuuccauccc uguggtttaa aaaaaaaaaa aaaaaaaaa     60 aaaaaaaa                                                            68

<210> SEQ ID NO 25
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 25
cauuccuggc uuuaauuuua cugguacagu uuctttaaaa aaaaaaaaaa aaaaaaaaaa    60
aaaaaa                                                              66

<210> SEQ ID NO 26
```

<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 26
ugccaaagag ugauuugagg gaatttaaaa aaaaaaaaaa aaaaaaaaaa aaaaaa     56

<210> SEQ ID NO 27
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 27
cccacucccu gacaugcugu caucauuucu utttaaaaaa aaaaaaaaaa aaaaaaaaaa     60
aaaa     64

<210> SEQ ID NO 28
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 28
uuuaaaucuu gugggguggc uccuucugau aaugcutttta aaaaaaaaaa aaaaaaaaaa     60
aaaaaaaaa     69

<210> SEQ ID NO 29
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 29
ucugcugucc cuguaauaaa cccgtttaaa aaaaaaaaaa aaaaaaaaaa aaaaaaa     57

<210> SEQ ID NO 30
<211> LENGTH: 56
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 30
gcuggaauaa cuucugcuuc uautttaaaa aaaaaaaaaa aaaaaaaaaa aaaaaa        56
```

CAPTURE PROBES IMMOBILIZABLE VIA L-NUCLEOTIDE TAIL

CROSS-REFERENCE TO RELATED APPLICATIONS

The present application is a continuation of U.S. application Ser. No. 13/823,551 filed Jun. 7, 2013, which is a US National Stage application of PCT/US2011/052050 filed Sep. 16, 2011, which itself is a nonprovisional and claims the benefit of 61/383,728 filed Sep. 16, 2010, each of which is incorporated by reference in its entirety for all purposes.

REFERENCE TO A SEQUENCE LISTING

This application includes an electronic sequence listing in a file named 430933CON_SEQLST.txt, created on Feb. 23, 2018 and containing 18,146 bytes, which is hereby incorporated by reference in its entirety for all purposes.

BACKGROUND

Detection of nucleic acids in a sample is useful in diagnostic, therapeutic, forensic, agricultural, food science applications and other areas. One technique for purifying a target polynucleotide, which is often used in diagnostic procedures, involves capturing a target polynucleotide onto a solid support. The solid support retains the target polynucleotide during one or more washing steps of the target polynucleotide purification procedure. The captured target sequence can be analyzed by various methods. One such method uses nucleic acid probes that hybridize to a target sequence. Probes can be designed to detect different target sequences such as those characteristic of microorganisms, viruses, human genes, plant or animal genes, and/or pathogenic conditions. Additional analysis techniques that benefit from captured target nucleic acids include, amplification assays, microarrays, sequencing assays, mass spectrometry of nucleic acids, and other techniques known in the art.

A target nucleic acid can be captured using a mediator or capture polynucleotide that hybridizes to bind both to a target nucleic acid and to a nucleic acid fixed to a solid support. The mediator polynucleotide joins the target nucleic acid to the solid support to produce a complex comprising a bound target nucleic acid. A labeled probe can be hybridized to the bound target and unbound labeled probe can be washed away from the solid support (see Stabinsky, U.S. Pat. No. 4,751,177).

Because hybridization proceeds more rapidly between nucleic acids that are both in solution compared to between one nucleic acid in solution and one immobilized nucleic acid, it is preferable in capturing a target nucleic acid using a capture probe that the capture probe hybridizes to the target nucleic before the capture probe is immobilized by binding to a support-bound polynucleotide. Such can be accomplished by performing the capture under first hybridization conditions in which the capture probe hybridizes to the target nucleic acid to for a target capture probe:target nucleic acid complex, and second hybridization conditions of reduced stringency in which the capture probe of the formed complex binds to an immobilized probe to form a further complex comprising immobilized probe:target capture probe:target nucleic acid (see Weisburg et al, U.S. Pat. No. 6,110,678). This type of assay is facilitated by designing the capture probe and immobilized probe to contain complementary homopolymer sequences of adenine and thymine. The melting temperature of hybrids formed between adenine and thymine is usually less than that formed between complementary sequences that include guanine and cytosine residues.

SUMMARY OF THE CLAIMED INVENTION

The invention provides methods of capturing a target nucleic acid. The methods involve contacting a target nucleic acid with a capture probe and an immobilized probe, the capture probe comprising a first segment that binds to the target nucleic acid and a second segment that binds to the immobilized probe, wherein the second segment of the capture probe and the immobilized probe comprise L-nucleic acids that can hybridize to one another, wherein the target nucleic acid binds to the first segment of the capture probe, and the second segment of the capture probe binds to the target, thereby capturing the target nucleic acid. Optionally, the first segment includes a D nucleic acid of at least 10 D-nucleobase units complementary to the target nucleic acid. Optionally, the D-nucleic acid comprises any of adenine-D-deoxyribose, guanine D-deoxyribose, thymine D-deoxyribose and cytosine D-deoxyribose. Optionally, the first segment includes a D-nucleic acid of 10-30 D-nucleobase units complementary to the target nucleic acid. Optionally, the first segment binds non-specifically to the target nucleic acid. Optionally, the first segment includes a random sequence of D-nucleobase units that binds nonspecifically to the target nucleic acid. Optionally, the second segment includes an L-nucleic acid of at least six L-nucleobase units complementary to an L-nucleic acid of at least six L-nucleobase units in the immobilized probe. Optionally, the second segment includes an L-nucleic acid of 10-30 L-nucleobase units complementary to an L-nucleic acid of 10-30 contiguous L-nucleobase units in the immobilized probe. Optionally, the L-nucleic acid of the second segment is a homopolymer and the L-nucleic acid of the immobilized probe constitutes a complementary homopolymer. Optionally, the homopolymer of the second segment is a homopolymer of adenine nucleobase units and the homopolymer of the immobilized probed is a homopolymer of thymine nucleobase units or vice versa. Optionally, the target nucleic acid is contacted with the capture probe and immobilized probe simultaneously. Optionally, the target nucleic acid is contacted with the capture probe before the immobilized probe. Optionally, the binding of the target nucleic acid to the capture probe occurs under first hybridization conditions and the binding of the capture probe to the immobilized probe occurs under second hybridization conditions. Optionally, the first conditions are more stringent than the second conditions. Optionally, the binding of the target nucleic acid to the capture probe and the binding of the capture probe to the immobilized probe occur under the same hybridization conditions. Optionally, the L-nucleic acids comprise any of adenine L-deoxyribose, guanine L-deoxyribose, cytosine L-deoxyribose or thymine L-deoxyribose joined by phosphodiester linkages. Optionally, the immobilized probe is immobilized to a magnetic bead. Optionally, the target nucleic acid is provide as a component of a sample and the method further comprising separating the captured target nucleic acid from other components of the sample. Optionally, the captured target nucleic acid is dissociated from the immobilized probe. Optionally, the target nucleic acid is amplified. The amplifying can be performed after dissociating the target nucleic acid from the capture probe. Optionally, the target nucleic acid is contacted with a detection probe and detecting the detection probe. Optionally, the target nucleic is contacted with the detection probe after dissociating the target nucleic acid from the capture probe. Optionally, the target nucleic acid is an HIV nucleic acid. Optionally, the L-nucleic acids are a homopolymer of adenine nucleobase units and a homopolymer of thymine nucleobase units and the sample includes mRNA or a nucleic acid derived therefrom.

The invention further provides a capture probe comprising a first segment of at least 10 D-nucleobase units and a second segment comprising a homopolymer of at least 10 L-nucleobase units. Optionally, the second segment is a homopolymer of adenine or thymine nucleobase units, preferably a homopolymer of thymine nucleobase units. The invention further provides an immobilized probe comprising a homopolymer of at least 10 L-nucleobase units linked to a support. Optionally the support is a magnetic particle. Optionally, the homopolymer is a homopolymer of thymine nucleobase units.

The invention further provides a kit comprising a capture probe comprising a first segment including a D-nucleic acid that binds to a target nucleic acid and a second segment including a homopolymeric L-nucleic acid and an immobilized probe comprising an L-nucleic acid comprising a complementary homopolymeric L-nucleic acid, wherein the capture probe and immobilized probe can hybridize to one another via hybridization of the complementary homopolymeric L-nucleic acids. Optionally, the homopolymeric L-nucleic acid is a homopolymer of adenine nucleobase units and the complementary homopolymeric L-nucleic acid is a homopolymer of thymine nucleobase units.

DEFINITIONS

Figure 1:
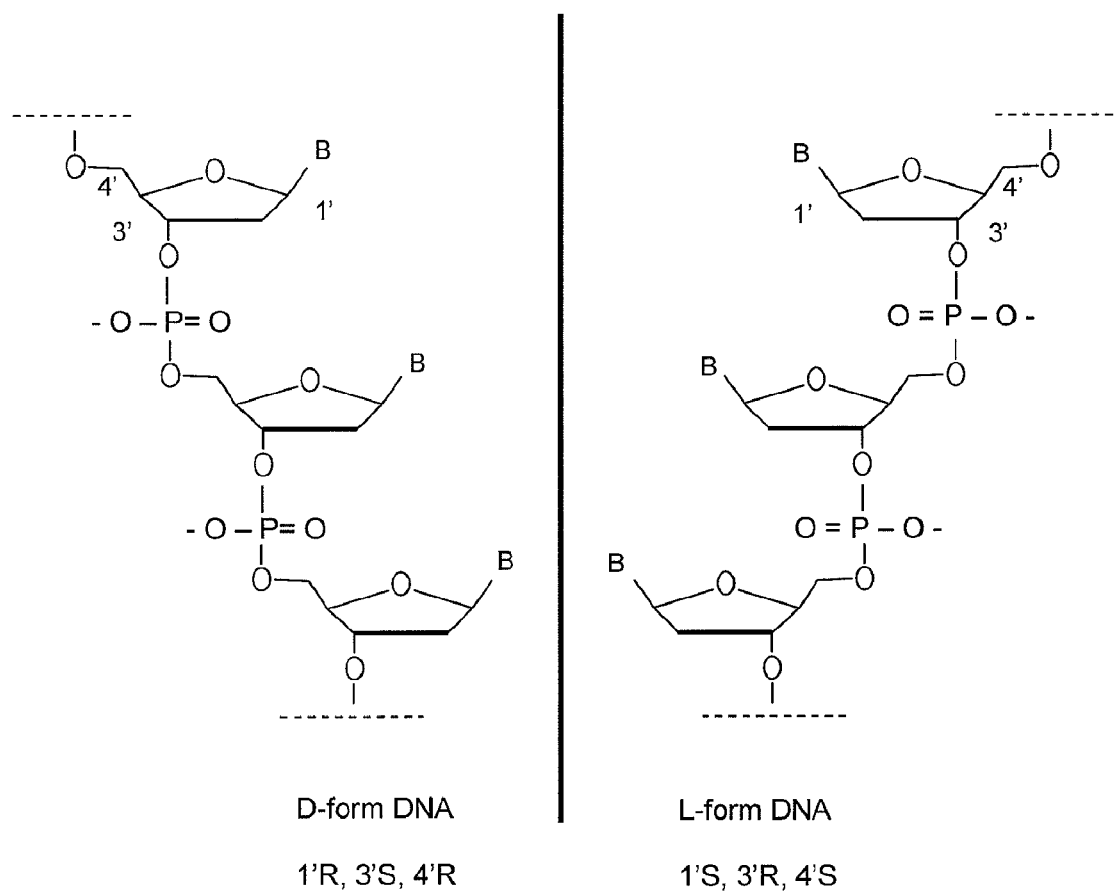
FIG. 1 compares D- and L-nucleic acids.

A nucleic acid refers to a multimeric compound comprising nucleotides or analogs that have nitrogenous heterocyclic bases or base analogs linked together to form a polymer, including conventional RNA, DNA, mixed RNA-DNA, and analogs thereof.

The nitrogenous heterocyclic bases can be referred to as nucleobases. Nucleobases can be conventional DNA or RNA bases (A, G, C, T, U), base analogs, e.g., inosine, 5-nitroindazole and others (The Biochemistry of the Nucleic Acids 5-36, Adams et al., ed., 11.sup.th ed., 1992; van Aerschott et al., 1995, Nucl. Acids Res. 23(21): 4363-70), imidazole-4-carboxamide (Nair et al., 2001, Nucleosides Nucleotides Nucl. Acids, 20(4-7):735-8), pyrimidine or purine derivatives, e.g., modified pyrimidine base 6H,8H-3,4-dihydropyrimido[4,5-c][1,2]oxazin-7-one (sometimes designated "P" base that binds A or G) and modified purine base N6-methoxy-2,6-diaminopurine (sometimes designated "K" base that binds C or T), hypoxanthine (Hill et al., 1998, Proc. Natl. Acad. Sci. USA 95(8):4258-63, Lin and Brown, 1992, Nucl. Acids Res. 20(19):5149-52), 2-amino-7-deaza-adenine (which pairs with C and T; Okamoto et al., 2002, Bioorg. Med. Chem. Lett. 12(1):97-9), N-4-methyl deoxygaunosine, 4-ethyl-2'-deoxycytidine (Nguyen et al., 1998, Nucl. Acids Res. 26(18):4249-58), 4,6-difluorobenzimidazole and 2,4-difluorobenzene nucleoside analogues (Kiopffer & Engels, 2005, Nucleosides Nucleotides Nucl. Acids, 24(5-7) 651-4), pyrene-functionalized LNA nucleoside analogues (Babu & Wengel, 2001, Chem. Commun. (Camb.) 20: 2114-5; Hrdlicka et al., 2005, J. Am. Chem. Soc. 127(38): 13293-9), deaza- or aza-modified purines and pyrimidines, pyrimidines with substituents at the 5 or 6 position and purines with substituents at the 2, 6 or 8 positions, 2-aminoadenine (nA), 2-thiouracil (sU), 2-amino-6-methylaminopurine, O-6-methyl guanine, 4-thio-pyrimidines, 4-amino-pyrimidines, 4-dimethylhydrazine-pyrimidines, and O-4-alkyl-pyrimidines (U.S. Pat. No. 5,378,825; PCT No. WO 93/13121; Gamper et al., 2004, Biochem. 43(31): 10224-36), and hydrophobic nucleobases that form duplex DNA without hydrogen bonding (Berger et al., 2000, Nucl. Acids Res. 28(15): 2911-4). Many derivatized and modified nucleobases or analogues are commercially available (e.g., Glen Research, Sterling, Va.).

A nucleobase unit attached to a sugar, can be referred to as a nucleobase unit, or monomer. Sugar moieties of a nucleic acid can be ribose, deoxyribose, or similar compounds, e.g., with 2' methoxy or 2' halide substitutions. Nucleotides and nucleosides are examples of nucleobase units.

The nucleobase units can be joined by a variety of linkages or conformations, including phosphodiester, phosphorothioate or methylphosphonate linkages, peptide-nucleic acid linkages (PNA; Nielsen et al., 1994, Bioconj. Chem. 5(1): 3-7; PCT No. WO 95/32305), and a locked nucleic acid (LNA) conformation in which nucleotide monomers with a bicyclic furanose unit are locked in an RNA mimicking sugar conformation (Venter et al., 2004, Biochemistry 43(42):13233-41; Hakansson & Wengel, 2001, Bioorg. Med. Chem. Lett. 11 (7):935-8), or combinations of such linkages in a nucleic acid strand. Nucleic acids may include one or more "abasic" residues, i.e., the backbone includes no nitrogenous base for one or more positions (U.S. Pat. No. 5,585,481).

A nucleic acid may include only conventional RNA or DNA sugars, bases and linkages, or may include both conventional components and substitutions (e.g., conventional RNA bases with 2'-O-methyl linkages, or a mixture of conventional bases and analogs). Inclusion of PNA, 2'-methoxy or 2'-fluoro substituted RNA, or structures that affect the overall charge, charge density, or steric associations of a hybridization complex, including oligomers that contain charged linkages (e.g., phosphorothioates) or neutral groups (e.g., methylphosphonates) may affect the stability of duplexes formed by nucleic acids.

An oligomer may contain a "random polymer" sequence that refers to a population of oligomers that are substantially the same in overall length and other characteristics, but in which at least a portion of the oligomer is synthesized by random incorporation of different bases for a specified length, e.g., a random assortment of all four standard bases (A, T, G, and C) in a DNA oligomer, or a random assortment of a few bases (U and G) in a defined portion of a larger oligomer. The resulting oligomer is actually a population of oligomers whose finite number of members is determined by the length and number of bases making up the random portion (e.g., 2.sup.6 oligomers in a population of oligomers that contains a 6-nt random sequence synthesized by using 2 different bases).

Complementarity of nucleic acids means that a nucleotide sequence in one strand of nucleic acid, due to orientation of its nucleobase groups, hydrogen bonds to another sequence on an opposing nucleic acid strand. The complementary bases typically are, in DNA, A with T and C with G, and, in RNA, C with G, and U with A. Complementarity can be perfect (i.e., exact) or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm of hybridized strands, or by empirical determination of Tm by using routine methods. Tm refers to the temperature at which a population of hybridization complexes formed between two nucleic acid strands are 50% denatured. At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41(% G+C), although other known Tm computations take into account nucleic acid structural characteristics.

"Hybridization condition" refers to the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment (e.g., Sambrook et al., Molecular Cloning, A Laboratory Manual, 2.sup.nd ed., pp. 1.90-1.91, 9.47-9.51, 11.47-11.57 (Cold Spring Harbor Laboratory Press, Cold Spring Harbor, N.Y., 1989)).

A "label" refers to a molecular moiety that is detectable or produces a detectable response or signal directly or indirectly, e.g., by catalyzing a reaction that produces a detectable signal. Labels include luminescent moieties (such as fluorescent, bioluminescent, or chemiluminescent compounds), radioisotopes, members of specific binding pairs (e.g., biotin and avidin), enzyme or enzyme substrate, reactive groups, or chromophores, such as a dye or particle that results in detectable color.

A "detection probe" is a nucleic acid or other molecule that binds specifically to a target sequence and which binding results, directly or indirectly, in a detectable signal to indicate the presence of the target sequence. A detection probe need not be labeled to produce a detectable signal, e.g., an electrical impulse resulting from binding the probe to its target sequence may be the detectable signal. A "labeled probe" is a probe that contains or is linked, directly or indirectly, to a label (e.g., Sambrook et al., Molecular Cloning, A Laboratory Manual, 2nd ed., Chapt. 10; U.S. Pat. No. 6,361,945, Becker et al.; U.S. Pat. No. 5,658,737, Nelson et al.; U.S. Pat. No. 5,656,207, Woodhead et al.; U.S. Pat. No. 5,547,842, Hogan et al.; U.S. Pat. No. 5,283,174, Arnold et al.; U.S. Pat. No. 4,581,333, Kourilsky et al.; U.S. Pat. No. 5,731,148, Becker et al.). For example, detection probes may include a non-nucleotide linker and a chemiluminescent label attached to the linker (U.S. Pat. Nos. 5,185,439, 5,585,481 and 5,639,604, Arnold et al.). Examples of detection probes include oligonucleotides of about 5 to 50 nucleotides in length having an attached label that is detected in a homogeneous reaction, e.g., one that uses differential hydrolysis of a label on a bound or unbound probe.

Detection probes can have a nucleotide sequence that is of the same or opposite sense as the a target sequence depending on the format of the assay. Detection probes can hybridize to the same or different segment of a target sequence as a capture probe. Some detection probes have an attached chemiluminescent marker, e.g., an acridinium ester (AE) compound (U.S. Pat. Nos. 5,185,439, 5,639,604, 5,585,481, and 5,656,744). In some detection probes, an acridinium ester label is attached to a central region of the probe near a region of A and T base pairs by using a non-nucleotide linker (U.S. Pat. Nos. 5,585,481 and 5,656,744, Arnold, et al.) which restricts the amines of the nucleotide bases on both sides of the AE and provides a site for intercalation. Alternatively, an AE label may be attached to the 3' or 5' terminus of the detection probe which is used in conjunction with a second oligomer that hybridizes adjacent to the detection probe on the target nucleic acid to restrict the effects of nearby amine contributed by the target nucleic acid. In some detection probes, an AE label at or near the site of a mismatch with a related non-target polynucleotide sequence, to permit discrimination between the related sequence and the target sequence that may differ by only one nucleotide because the area of the duplex around the mismatch site is sufficiently destabilized to render the AE on the probe hybridized to the related non-target sequence susceptible to hydrolysis degradation. HIV 1 and HCV may be detected using a modified form of the commercial PROCLEIX® HIV-1/HCV Assay from Gen-Probe. The modification involves replacing the D-polyA and D-polyT sequences in capture and immobilized probes with L-poly A and L-poly-T, respectively.

Specific binding of a capture probe to a target nucleic or target nucleic acids means binding between a single defined sequence in the first segment of a capture probe and an exactly or substantially complementary segment on target nucleic acid(s) to form a stable duplex. Such binding is detectably stronger (higher signal or melting temperature) than binding to other nucleic acids in the sample lacking a segment exactly or substantially complementary to the single defined capture probe sequence. Non-specific binding of a capture probe to target nucleic acids means that the capture probe can bind to a population of target sequences that do not share a segment having exact or substantial complementarity to a single defined capture probe sequence. Such can be achieved by for example using a randomized sequence in the first segment of the capture probe.

Lack of binding as between an L-nucleic acid and D-nucleic acid can be manifested by binding indistinguishable from nonspecific binding occurring between a randomly selected pair of nucleic acids lacking substantial complementarity but of the same length as the L and D nucleic acid in question. Lack of binding between an L-nucleic acid and D-nucleic acid can also be manifested by lack of a detectable TM and/or capture of less than 1% of a target nucleic acid or a signal of captured target indistinguishable within experimental error from that captured by a control lacking a capture probe when the L-nucleic acid and D-nucleic acid are used to pair with one another in the capture probe and immobilized probe (or vice versa).

"Homogeneous detectable label" refers to a label whose presence can be detected in a homogeneous manner depending on whether the label is bound or unbound to a target. A homogeneous detectable label can be detected in a "homogeneous reaction" without physically separating unbound forms of the label from the mixture before the detection step. A homogeneous reaction may occur in solution or on a support such as a microarray, biochip, or gene chip. Preferred homogeneous detectable labels and conditions for their detection have been described previously in detail (U.S. Pat. No. 5,283,174, Arnold et al.; U.S. Pat. No. 5,656,207, Woodhead et al.; U.S. Pat. No. 5,658,737, Nelson et al.).

A "chimeric capture probe" serves to join a target nucleic acid and an immobilized probe by hybridization of complementary sequences. A chimeric target capture probe is sometimes referred to as a capture probe. A chimeric capture probe includes a first segment including a target-complementary region of sequence and a second segment for attaching the capture probe, or a hybridization complex that includes the capture probe, to an immobilized probe. The first segment can be configured to substantially complementary to a specific target nucleic acid sequence so that a first segment and a target nucleic acid can hybridize to form a stable duplex (i.e., having a detectable melting point) under hybridizing conditions, such as described in the Examples. Alternatively, the first segment can be configured to non-specifically bind to nucleic acid sequences in a sample under hybridizing conditions (see WO 2008/016988). The second segment includes a region of sequence that is complementary to a sequence of an immobilized probe. Preferably, a chimeric capture probe includes a nucleic acid homopolymer (e.g., poly-A or poly-T) that is covalently attached to the target-complementary region of the capture probe and that hybridizes under appropriate conditions to a complementary homopolymer of the immobilized probe (e.g., poly-T or poly-A, respectively) as previously described (U.S. Pat. No. 6,110,678 to Weisburg et al.). Capture probes may further comprise a third segment that acts as a closing sequence to inactivate unbound target capture probes in a capture reaction. This third segment can flank the first segment opposite the second segment (e.g., capture sequence:target hybridizing sequence:closing sequence) or it can flank the second segment opposite the first segment (e.g., closing sequence: capture sequence:target hybridizing sequence). See WO 2006/007567 and US 2009-0286249.

"Separating" or "isolating" or "purifying" refers to removing one or more components from a complex mixture, such as a sample. Preferably, a separating, isolating or purifying step removes at least 70%, preferably at least 90%, and more preferably about 95% of the target nucleic acids from other sample components. A separating, isolating or purifying step may optionally include additional washing steps to remove non-target sample components. It is understood that at least X % refers to a range from X % to 100% inclusive of all whole and partial numbers (e.g., 70%, 82.5%, etc.)

"Release" of a capture hybrid refers to separating one or more components of a capture hybrid from each other, such as separating a target nucleic acid from a capture probe, and/or a capture probe from an immobilized probe. Release of the target nucleic acid strand separates the target from other components of a capture hybrid and makes the target available for binding to a detection probe. Other components of the capture hybrid may remain bound, e.g., the capture probe strand to the immobilized probe on a capture support, without affecting target detection.

Sensitivity is the proportion of true positives correctly identified as such (e.g. the percentage of infected patients correctly identified as having the infection). Specificity measures the proportion of true negatives which are correctly identified (e.g. the percentage of uninfected patients who are correctly identified as not having the infection.)

DETAILED DESCRIPTION

I. General

The invention provides chimeric target capture probes comprising first segments and second segments, wherein the capture probes are immobilizable to a support bearing an immobilized probe that is complementary to the second segment, and wherein the complementary portions of the second segment and the immobilized probe comprise left-handed nucleobase units forming an L-nucleic acid. L-nucleic acids are not capable of hybridizing to natural (i.e., D-) nucleic acids. Employing the chimeric capture probe with a D-nucleic acid first segment and an L-nucleic acid second segment for immobilization to an L-nucleic acid containing immobilized probe enables more specific capture of an intended target nucleic acid. For example, mRNAs, non-target virus sequences, or other such unintended non-target nucleic acid sequences can be prevented from binding to L-(polyT) particles via their comprised polyA sequences (either terminal or internal). This is particularly useful for specific capture of nucleic acids containing poly-A sections using a poly-A/poly-T capture configuration (e.g., U.S. Pat. No. 6,110,678) (e.g., fragmented genomic loci, mRNAs or viral nucleic acids (i.e. to prevent unintended capture of other loci that contain strings of polyA)).

The capture probes of the current invention are useful for capturing a target nucleic acid from a sample. The L-nucleic acid in the tail of the capture probe bind to the complementary L-nucleic acid in the immobilized probe with similar affinity as would otherwise equivalent D-nucleic acids. However, the L-nucleic acid of the capture probe tail and immobilized probes lack affinity for D-nucleic acids present in the in the sample containing the target nucleic acid. Accordingly, binding of nucleic acids in the sample directly to immobilized probe rather than via the capture probe as an intermediate can be eliminated. Binding of the capture probe's second segment to nucleic acids in the sample can therefore also be eliminated. Avoiding direct binding of nucleic acids to the immobilized probe and/or to the capture probe's second segment offers advantages in increasing the sensitivity and/or specificity of analytical techniques that use the captured target nucleic acids. The purity of target nucleic acid is particularly advantageous for subsequent sequencing analyses, particularly by methods involving massively parallel sequencing of multiple different target nucleic acids including variants. Such methods of sequencing include single-molecule real time methods discussed further below. The methods are particularly useful when homopolymers of adenine and thymine are used in the capture probe tail and immobilized probe and the sample contains poly-A and/or poly-T containing nucleic acids (for example a sample containing mRNA or cDNA, viral RNA, human nucleic acids, mitochondrial DNA, genomic DNA or a nucleic acid derived by template-directed synthesis thereof) thus allowing elimination of binding of poly-A or poly-T nucleic acids in the sample to complementary sequences in the capture probe second segment and in the immobilized probe.

Captured target nucleic acids are useful in a number of analytical techniques, including among others, amplification assays (e.g., the PROCLEIX HIV-1/HCV Assay), base composition determination by mass spectrometry, microarray identification and nucleic acid sequencing assays. For each of these analytical techniques, the nucleic acids entering the assay have a direct impact on the information derived therefrom. The presence of non-target nucleic acids in an assay provides misinformation into the system that then complicates or even makes impossible a proper interpretation of the resulting data. Misinformation includes false positive signals, loss of robustness and sensitivity in the assay, and ambiguous results. Target nucleic acids captured using the compositions and methods of the current invention are more suitable for subsequent analyses compared to nucleic acids isolated by prior methods.

II. L-Nucleic Acid

Nucleic acids existing in nature are D-nucleic acids formed from D-nucleotides. An L-nucleic acid is the enantiomeric form of a D-nucleic acid. The source of stereoisomerism in a nucleic acid resides in the sugar moiety of each monomeric unit forming the nucleic acid (as illustrated in FIG. 1). Except for the stereoisomerisms at the sugar moiety of each monomeric unit, D and L-nucleic acids and their monomeric units are closely analogous. Thus, for example, the sugar moieties of an L-nucleic acid can be linked to the same nucleobases (i.e., adenine, guanine, cytosine, thymine and uracil) as occur in natural DNA or RNA, or any of the many known analogs of these nucleobases. The sugar moiety of L-nucleic acids can be ribose or deoxyribose or similar compounds (e.g., with 2'-methoxy or 2' halide substitutions). The sugar moieties can be linked by sugar phosphodiester linkages as in D-nucleic acids or by any of the analog linkages that have been used with D-nucleic acids, such as phophorothioate or methylphosphonate linkages or peptide-nucleic acid linkages.

L-nucleotides incorporating at least the conventional nucleobases (i.e., A, C, G, T and U) are commercially available in the phosphoramidite form suitable for solid phase synthesis (e.g., ChemGenes Corporation (Wilmington, USA). L-nucleic acids can be synthesized from L-nucleotides using the same solid phase synthesis procedures as are used for D-nucleic acids (e.g., an ABI synthesizer and standard synthesis protocols). L-nucleotides can also be linked to D-nucleotides by a conventional coupling cycle (see Hauser et al., Nucleic Acids Research, 2006, Vol. 34, No. 18 5101-5111 (2006), thus permitting synthesis of a chimeric nucleic acid having one segment in D-nucleic acid form and the other in L-nucleic form.

L-nucleic acids hybridize to one another according to analogous principles to D-nucleic acids (e.g., by formation of Watson-Crick or Hoogstein bonds) and have similar stability to hybrids of D-nucleic acids. The duplex formed from L-nucleic acids is a left-handed helix whereas that formed from D-nucleic acids is a right handed helix. Although L-nucleic acids can hybridize to each other, as further illustrated by the Examples, L-nucleic acids and particularly polyA or polyT L-nucleic acids have no ability to hybridize to a complementary segment of a poly A or polyT D-nucleic acid.

III. Capture Probes

The invention employs chimeric target capture probes having at least first and second segments. The first segment binds to a target nucleic acid either specifically or nonspecifically (see U.S. Pat. No. 6,110,678 and WO 2008/016988). The second segment, sometimes known as a tail, binds to an immobilized probe and thus serves to capture the target nucleic bound to the capture probe to a support linked to an immobilized probe. Capture probes are typically provided in single-stranded form, or if not, are denatured to single-stranded form before or during use (see WO 2006/007567 and US 2009-0286249).

The first segment of the chimeric capture probe is typically designed to bind to a target nucleic acid sequence of interest. In some capture probes, the first segment is designed to bind to a segment within a particular target nucleic acid and not to (or at least with substantially reduced affinity) to other nucleic acids lacking this segment that are present in the sample. In other capture probes, the first segment is designed to bind to a class of target nucleic acids (e.g., any DNA molecule) and does not necessarily substantially discriminate between individual target nucleic acids within the class (e.g., by use of a randomized sequence).

For the first segment to bind to a particular target nucleic acid sequence of interest, the first segment can be designed to include a D-nucleic acid that is substantially and preferably exactly complementary to a corresponding segment of the target nucleic acid. The D-nucleic acid of such a first segment preferably includes at least 6, 10, 15 or 20 nucleobase units (e.g., nucleotides). For example, the D-nucleic acid can contain 10-50, 10-40, 10-30 or 15-25 nucleobase units (e.g., D-nucleotides) complementary to corresponding D-nucleotides in the target nucleic acid. Here, as elsewhere in the application, ranges for contiguous nucleic acid sequences are fully inclusive of all whole numbers defining or within the range (10, 11, 12, 13 . . . 47, 48, 49, 50).

For the first segment to bind nonspecifically to nucleic acids without necessarily substantially discriminating between different sequences within a class, the first segment can include a random polymer sequence made up of all four standard DNA bases (guanine (G), cytosine (C), adenine (A) and thymine (T)) or all four standard RNA bases (G, C, A, and uracil (U)) (see US 2008/0286775) The random sequence can also include one or more base analogs (e.g., inosine, 5-nitroindole) or abasic positions in the random polymer sequence. Such a random polymer sequence can contain one or more sequences of poly-(k) bases, i.e., a random mixture of G and U or T bases (e.g., see Table 1 of WIPO Handbook on Industrial Property Information and Documentation, Standard ST.25 (1998)). Sequences that include G and U/T bases can be chosen for their "wobble" property, i.e., U/T binds G or A, whereas G binds C or U/T. A capture probe having a first segment synthesized with a random polymer sequence is in fact a finite population of oligonucleotides that contain different random polymer sequences made up of the bases included during the synthesis of the random portion. For example, a population of nonspecific capture probes that include a 15 nt random polymer sequence made up of G, C, A and T consists of $4^{15}$ members. The first segment can be designed to bind to DNA sequences preferentially relative to RNA or vice versa (see US 2008-0286775).

The second segment is designed to bind to an immobilized probe. The second segment includes an L-nucleic acid that is substantially and preferably exactly complementary to an L-nucleic acid present in the immobilized probes. The L-nucleic acid of the capture probe preferably includes at least six nucleobase units (e.g., L-nucleotides) and preferably 10-50, 10-40, 10-10 or 15-25 nucleobase units (e.g., L-nucleotides). Ranges for contiguous nucleic acid sequences are fully inclusive of all whole numbers (10, 11, 12, 13 . . . 47, 48, 49, 50) defining or within the range. The L-nucleic acid of the capture probe is preferably a homopolymer or combination of two homopolymers in tandem, and more preferably polyA and/or polyT (e.g. $(T)_{0-5}/(A)_{10-40}$, ranges being inclusive of all whole numbers defining or within the range). The term "poly-A" is used interchangeably with homopolymer of adenine nucleobase units, or sometimes simply a homopolymer of adenines. Likewise the term "poly-T" is used interchangeably with homopolymer of thymine nucleobase units or sometimes simply a homopolymer of thymines. A preferred L-nucleic acid is or includes a homopolymer of 30 adenines. The length of the L-nucleic acid (i.e., number of nucleobase units) in the capture probe may or may not be the same as the length of the L-nucleic acid in the immobilized probe.

The melting temperature of the duplex formed between the L-nucleic acid of the capture probe and L-nucleic acid of the immobilized probe preferably has a lower melting temperature than the duplex formed between the D-nucleic acid of the first segment of the capture probe and the target nucleic acid. The melting temperatures of both duplexes can be calculated by conventional equations relating base composition and length of a duplex to its melting temperature as discussed above. Selection of polyA or polyT homopolymers for the L-nucleic acids of the capture and immobilized probes tends to confer a lower melting temperature than that for a duplex formed between the first segment of the capture probe and the target nucleic acid because the latter duplex usually also contains some C-G pairings, which confer greater stability on a duplex than A-T pairings. A lower melting temperature of the duplex formed between the second segment of the capture probe and the immobilized probe than the duplex formed between the first segment of the capture probe and the target nucleic acid is advantageous in allowing the hybridization to be performed under conditions of higher stringency in which the capture probe first hybridizes to the target nucleic acid and lower stringency in which the capture probe now hybridizes to the target nucleic acid hybridizes to the immobilized probe. When performed in this order, both capture probe and target nucleic acid are in solution when they hybridize in which conditions, hybridization takes place with much faster kinetics.

The capture probe may or may not include additional segments as well as the first and second segments mentioned above. For example, the D-nucleobase units of the first segment and L-nucleobase units of the second segment can be directly connected by a phosphodiester bond (or any of the analogs thereof discussed above) or can be separated by a short spacer or linker region, which may include nucleotides, or other molecules, such as PEG typically found in linkers. For example, if the second segment is a polyA homopolymer, the first and second segments can be connected by one or more (e.g., three) thymine residues (which can be L or D enantiomers). In some probes, the first and second segments are connected by 0-5 thymine residues. A capture probes can also include a third segment such that the first segment is flanked by the second and third segments. In such an arrangement, the third segment can include an L-nucleic acid complementary to the L-nucleic acid in the second segment, such that the capture probe is capable of self-annealing to form a stem-loop structure in which the second and third segments are annealed as a stem and the first segment forms a loop in between. Such a stem loop structure can only form when the first target nucleic acid is not hybridized with its target nucleic acid. Such an arrangement can be useful in reducing the ability of a capture probe to hybridize with an immobilized probe before the capture probe has bound to its target nucleic acid and in reducing competition between unhybridized capture probe and a detection probe used to detect the target nucleic acid (see US 20060068417).

Multiple different capture probes can be used in combination in the same reaction. In this case, the different capture probes typically have different first segments complementary to different target nucleic acids or different segments within the same target nucleic acid, and the identical second segments, so they can bind immobilized probes having the complementary sequences to these second segments. Use of multiple different capture probes can be useful in capturing a population of related target sequences that may be present in a sample, for example, sequence and/or length variants. The number of different capture probes can be at least 1, 2, 5, 10, 20, 50 or 100, for example, 1-100 or 2-50 or 3-25, inclusive of all whole numbers defining or within the range.

IV. Immobilized Probe

An immobilized probe includes an L-nucleic acid joined directly or indirectly to a support. As indicated in the description of the capture probe, the L-nucleic acid is substantially or preferably exactly complementary to an L-nucleic acid in the capture probe, although may or may not be the same length (number of nucleobase units) as the L-nucleic acid in the capture probe. The L-nucleic acid in the immobilized probe preferably contains at least six contiguous L-nucleobase units (e.g., L-nucleotides) and can contain for example 10-45 or 10-40 or 10-30 or 10-25 or 15-25, inclusively, L-nucleobase units, any range being inclusive of all whole numbers defining or within the range. The L-nucleic acid is preferably a homopolymer, and more preferably a homopolymer of adenine or thymine. A preferred form of immobilized probe is or includes a homopolymer of 14 thymine residues for use in combination with a capture probe including a second segment with a homopolymer of adenine residues. The nucleic acid moiety of an immobilized probe is typically provided in single-stranded form, or if not, is denatured to single-stranded form before or during use.

Any of a variety of materials may be used as a support for the immobilized probes, e.g., matrices or particles made of nitrocellulose, nylon, glass, polyacrylate, mixed polymers, polystyrene, silane polypropylene, and magnetically attractable materials. Monodisperse magnetic spheres are a preferred support because they are relatively uniform in size and readily retrieved from solution by applying a magnetic force to the reaction container, preferably in an automated system. An immobilized probe may be linked directly to the capture support, e.g., by using any of a variety of covalent linkages, chelation, or ionic interaction, or may be linked indirectly via one or more linkers joined to the support. The linker can include one or more nucleotides of either D or L-enantiomeric forms not intended to hybridize to the capture probe but to act as a spacer between the L-nucleic acid of the immobilized probe and its support.

V. Target Nucleic Acid

A target nucleic acid refers to a nucleic acid molecule or class of nucleic acid molecules that is or may be present within a sample. A target nucleic acid may be a particular type of nucleic acid (e.g., a particular mRNA present in a heterogeneous mixture of mRNA) or can represent a class of molecules (e.g., any DNA or any mRNA present in a sample). A target nucleic acid includes a segment (target segment) that hybridizes with the first segment on the capture probe to form a stable duplex between D-nucleic acids. The target segment can be the same or substantially the same length as the D-nucleic acid of the first segment of the capture probe and exactly or substantially complementarity to this nucleic acid. The target segment can be only a small fraction of the total length of a target nucleic acid. For example, a target nucleic acid can be several thousand nucleotides long and a target segment can be for example, only 10-30 of these nucleotides. A target nucleic acid can exist in different forms, i.e., single-stranded, double-stranded, triple-stranded, or mixtures thereof, such as in a partially double-stranded hairpin structure or partially double-stranded duplex structure, and a target segment can be present on any strand (sense or anti-sense) of the structure. A target nucleic acid can be RNA (e.g., viral RNA, micro RNA, mRNA, cRNA, rRNA, hnRNA or DNA (genomic or cDNA) among others. The target nucleic acid can be from a pathogenic microorganism, such as a virus, bacteria or fungus, or can be endogenous to a patient. A target nucleic acid can be synthetic or naturally occurring. A target nucleic acid can range in length from at least about ten nucleotides to more than 1000 nucleotides or up to 10,000 nucleotides or even greater than 10,000 nucleotides. Target nucleic acids having 25-10,000 nucleotides are common.

Viral nucleic acids (e.g., genomic, mRNA or cDNA) form a useful target for detection or analyses of viruses. Nucleic acid based detection is particularly useful soon after infection, when transcription and production of viral proteins and antibodies may not have occurred to a detectable extent for an immunoassay. Some examples of viruses that can be detected include HIV, hepatitis (A, B, or C), herpes virus (e.g., VZV, HSV-1, HAV-6, HSV-II, CMV, and Epstein Barr virus), adenovirus, XMRV, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, MLV-related Virus, papillomavirus, molluscum virus, poliovirus, rabies virus, JC virus and arboviral encephalitis virus.

Analysis of viral nucleic acids is also useful for analyzing drug resistance. Viruses mutate rapidly so that a patient is often infected with a heterogeneous population of viral nucleic acids, which changes over time. Deconvolution of the population to detect individual variants allows detection of drug resistant mutations and their change over time, thus allowing treatment regimes to be customized to take into account the drug resistance of strains infecting a particular patient.

Human nucleic acids are useful for diagnosing diseases or susceptibility towards disease (e.g., cancer gene fusions, BRACA-1 or BRAC-2, p53, CFTR, cytochromes P450), for genotyping (e.g., forensic identification, paternity testing, heterozygous carrier of a gene that acts when homozygous, HLA typing), determining drug efficacy on an individual (e.g., companion diagnostics) and other uses.

rRNA is particularly useful for detecting and/or typing pathogenic bacteria. Examples of such bacteria include *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, Lymes disease bacteria, streptococci, or *neisseria*.

VI. Sample

A "sample" or "biological sample" refers to any composition or mixture in which a target nucleic acid of interest may be present, including plant or animal materials, waste materials, materials for forensic analysis, environmental samples, and the like. A biological sample includes any tissue, cell, or extract derived from a living or dead organism which may contain a target nucleic acid, e.g., peripheral blood, bone marrow, plasma, serum, biopsy tissue including lymph nodes, respiratory tissue or exudates, gastrointestinal tissue, urine, feces, semen, or other body fluids. Samples of particular interest are tissue samples (including body fluids) from a human or an animal having or suspected of having a disease or condition. Other samples of interest include industrial samples, such as for water testing, food testing, contamination control, and the like.

Sample components may include target and non-target nucleic acids, and other materials such as salts, acids, bases, detergents, proteins, carbohydrates, lipids and other organic or inorganic materials.

A sample may or may not be subject of processing to purify or amplify a target nucleic acid before performing the target capture assay described below. It is not, for example, necessary to perform a column binding of elution of nucleic acids. Such a step concentrates and purifies nucleic acids but also can lose a large proportion of the sample. Further processing can include simple dilution of a biological fluid with a lysing solution to more complex methods that are well known in the art (e.g., Su et al., J. Mol. Diagn. 2004, 6:101-107; Sambrook, J. et al., 1989, Molecular Cloning, A Laboratory Manual, 2nd ed., pp. 7.37-7.57; and U.S. Pat. Nos. 5,374,522, 5,386,024, 5,786,208, 5,837,452, and 6,551,778). Typically, a sample containing a target nucleic acid is heated to inactivate enzymes in the sample and to make the nucleic acids in the sample single-stranded (e.g., 90-100° C. for 2-10 min, then rapidly cooling to 0-5° C.).

VII. Target Capture Assay

A target capture assay is performed using one or more chimeric capture probes of the invention, an immobilized probe, a sample and a suitable medium to permit hybridization of the capture probe to the target nucleic acid and of capture probe to the immobilized probe. Usually, the target sample is heated before performing the assay to denature any nucleic acids in double-stranded form. The components can be mixed in any order. For example the capture probe can be added to the sample and hybridized with the target nucleic acid in the sample before adding the immobilized probe. Alternatively, the capture probe can already be hybridized to the immobilized probe before supplying these two probes to the assay mix. However, for an automated assay, it is preferable to minimize the number of adding steps by supplying the capture probe and immobilized probe at the same or substantially the same time. In this case, the order of hybridization can be controlled by performing a first hybridization under conditions in which a duplex can form between the capture probe and the target nucleic acid but which exceeds the melting temperature of the duplex that would form between the capture probe and immobilized probe, and then performing a second hybridization under conditions of reduced stringency. Stringency can most easily be reduced by lowering the temperature of the assay mix.

Following formation of the target nucleic acid:capture probe:immobilized probe hybrid (the capture hybrid complex) can be isolated away from other sample components by physically separating the capture support using any of a variety of known methods, e.g., centrifugation, filtration, or magnetic attraction of a magnetic capture support. To further facilitate isolation of the target nucleic acid from other sample components that adhere non-specifically to any portion of the capture hybrid, the capture hybrid may be washed one or more times to dilute and remove other sample components. Washing may be accomplished by dissociating the capture hybrid into its individual components in an appropriate aqueous solution (e.g., a solution containing Tris and EDTA. See e.g., U.S. Pat. No. 6,110,678) and appropriate conditions (e.g., temperature above the Tm of the components) and then readjusting the conditions to permit reformation of the capture hybrid. However, for ease of handling and minimization of steps, washing preferably rinses the intact capture hybrid attached to the capture support in a solution by using conditions that maintain the capture hybrid.

Next the target nucleic acid can be released from the capture hybrid, although amplification and/or detection can alternatively be performed while the target nucleic acid is still bound to the capture probe. Release of the target or capture hybrid components can be performed by several methods, such as, e.g., changing one or more conditions to promote dissociation of components (e.g., heating above Tm, changing salt concentrations, adding denaturants or competitive binding moieties to the mixture, or by including compounds in the reaction that improve hybridization, such as imidazole compounds), or by using other conventional methods such as strand displacement. Typically, a simple heating step is performed to melt the target and capture probe strands, e.g., in an aqueous solution of low ionic strength, at 90-100° C. for 5 min, followed by rapid cooling to 0-5° C. Other components of the capture hybrid may be released (e.g., capture probe), but only the target nucleic acid must be made available to bind to the detection probe. The soluble phase containing the released target nucleic acid may be separated from other components of the mixture (e.g., capture support and/or unbound capture probes) but this is not critical because the capture probe strand is of the same sense as the detection probe and, therefore, will not interfere with the detection probe binding to the target.

Preferably, capture of the target nucleic acid with washing if performed, removes at least 70%, preferably at least 90%, and more preferably about 95% of the target nucleic acids from other sample components.

The target nucleic acid can optionally be subject to a reverse transcription or amplification step, which can be performed with or without release of the target nucleic acid from the capture complex. PCR amplification is described in PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. No. 4,683,202. Other suitable amplification methods include the ligase chain reaction (LCR) (see Wu and Wallace, Genomics 4, 560 (1989), Landegren et al., Science 241, 1077 (1988), transcription amplification (Kwoh et al., Proc. Natl. Acad. Sci. USA 86, 1173 (1989)), and self-sustained sequence replication (Guatelli et al., Proc. Nat. Acad. Sci. USA, 87, 1874 (1990)) and nucleic acid based sequence amplification (NASBA).

A detection step can be performed in soluble phase by adding a detection probe directly to the soluble phase containing the released target nucleic acid and incubating the mixture in hybridization conditions suitable for binding the detection probe and target sequences (e.g., adding salts to the soluble phase to make a solution of suitable ionic strength and incubating at 25-60° C.). The detection probe can optionally be designed to be complementary or substantially complementary to the same segment of the target nucleic acid as the capture probe. Although the capture probe is released into solution it will not hybridize to the detection probe because the capture and detection probe oligomers are strands of the same sense. However, the released capture probe can compete with the detection probe for hybridization to the target nucleic acid. Thus, the detection probe is preferably provided in excess or designed to exhibit higher affinity (compared to the capture probe) for the target nucleic acid by virtue of the detection probe's length and/or structural modifications (e.g., backbone). For example, the detection probe can have a longer target-complementary sequence than the capture probe's target-complementary sequence. Optionally, if the capture probe includes a third segment capable of intramolecular duplex formation with the second segment, intramolecular hybridization can form a hairpin form of the capture probe decreasing its ability to compete with a detection probe in subsequent steps. The detection probe can also be designed to bind to a different segment of the same target nucleic acid than the capture probe in which case the capture probe does not compete with the detection probe for binding to the target nucleic acid. After the detection probe binds to the target nucleic acid to form the detection hybrid, a signal from the hybrid is detected to indicate the presence of the target in the tested sample. Optionally, unbound detection probe can be removed before signal detection. However, the detection hybrid is preferably detected in a homogeneous reaction to avoid having to separate the unbound probes before signal detection from the bound probes (e.g., as described in U.S. Pat. Nos. 5,283,174, 5,639,604, 5,948,899, 5,658,737, 5,756,709, 5,827,656, and 5,840,873). Detection of a signal from the detection hybrid indicates the presence of the target nucleic acid in the sample.

Optionally, one or more additional oligomers may bind to the target nucleic acid in the detection step to facilitate binding the detection probe and/or producing a detectable signal. Such additional oligomers include, e.g., helpers, competitive probes for cross-reacting non-target sequences, or an oligomer that brings another component used in signal production (e.g., enzyme, substrate, catalyst, or energy emitter) into proximity with the detection probe (U.S. Pat. No. 5,030,557, Hogan et al.; U.S. Pat. No. 5,434,047, Arnold; and U.S. Pat. No. 5,928,862, Morrison).

As well as or instead of performing a simple detection step that may detect the presence and/or amount of a target nucleic acid in a sample, a captured target nucleic acid can also be subject to a more detailed analysis, for example, to detect mutations that may be present in a sample. The capture of target nucleic acid can be coupled to several different formats of so-called next generation and third generation sequencing methods. Such methods can sequence millions of target templates in parallel. Such methods are particularly useful when the target nucleic acid is a heterogeneous mixture of variants, such as is often the case in a sample from a patient infected with a virus, such as HIV. Among the many advantages, sequencing variants in parallel provides a profile of drug resistant mutations in the sample, even drug mutations present in relatively minor proportions within the sample.

Some next generation sequence methods amplify by emulsion PCR. A target nucleic acid immobilized to beads via a capture probe provides a suitable starting material for emulsion PCR. The beads are mixed with PCR reagents and emulsion oil to create individual micro reactors containing single beads (Margulies et al., Nature 437, 376-80 (2005)). The emulsion is then broken and the individual beads with amplified DNA are sequenced. The sequencing can be pyrosequencing performed for example using a Roche 454 GS FLX sequencer (454 Life Sciences, Branford, Conn. 06405). Alternatively, sequencing can be ligation/detection performed for example using an ABI SOLiD Sequencing System (Life Technologies, Carlsbad, Calif. 92008). In another variation, target nucleic acids are eluted from the capture probe and immobilized in different locations on an array (e.g., the HiScanSQ (Illumina, San Diego, Calif. 92121)). The target nucleic acids are amplified by bridge amplification and sequenced by template-directed incorporation of labeled nucleotides, in an array format (Illumina). In another approach, target nucleic acids are eluted from the capture probe and single molecules are analyzed by detecting in real-time the incorporation nucleotides by a polymerase. The nucleotides can be labeled nucleotides that release a signal when incorporated (e.g., Pacific Biosciences, Eid et al., Sciences 323 pp. 133-138 (2009) or unlabeled nucleotides, wherein the system measures a chemical change upon incorporation (e.g., Ion Torrent Personal Genome Machine (Guilform, Conn. 94080)). If labeled, different nucleotides can have the same or different labels as each other.

Although captured target nucleic acids can be sequenced by any technique, third generation, next generation or massively parallel methods offer considerable advantages over traditional techniques. Two traditional techniques for sequencing DNA are the dideoxy termination method of Sanger (Sanger et al., PNAS USA, 74: 5463 (1977)) and the Maxam-Gilbert chemical degradation method (Maxam and Gilbert, PNAS USA, 74: 560 (1977)). Both methods deliver four samples with each sample containing a family of DNA strands in which all strands terminate in the same nucleotide. Ultrathin slab gel electrophoresis, or more recently capillary array electrophoresis is used to resolve the different length strands and to determine the nucleotide sequence, either by differentially tagging the strands of each sample before electrophoresis to indicate the terminal nucleotide, or by running the samples in different lanes of the gel or in different capillaries. Both the Sanger and the Maxam-Gilbert methods are labor- and time-intensive, and require extensive pretreatment of the DNA source.

The concept of sequencing DNA by synthesis without using electrophoresis was first revealed in 1988 (Hyman, Analytical Biochemistry, 174: 423 (1988)) and involves detecting the identity of each nucleotide as it is incorporated into the growing strand of DNA in polymerase reaction. Such a scheme coupled with the chip format and laser-induced fluorescent detection markedly increases the throughput of DNA sequencing projects. Several groups have described such systems with an aim to construct an ultra high-throughput DNA sequencing procedure (see. e.g., Cheeseman, U.S. Pat. No. 5,302,509, Metzker et al., Nucleic Acids Res. 22: 4259 (1994)). The pyrosequencing approach that employs four natural nucleotides (comprising a base of adenine (A), cytosine (C), guanine (G), or thymine (T)) and several other enzymes for sequencing DNA by synthesis is now widely used for mutation detection (Ronaghi, Science 281, 363 (1998); Binladin et al., PLoS ONE, issue 2, e197 (February 2007); Rehman et al., American Journal of Human Genetics, 86, 378 (March 2010); Lind et al, Human Immunology 71, 1033-1042 (2010); Shafer et al., J Infect Dis. 1; 199(5):610 (2009)). In this approach, the detection is based on the pyrophosphate (PPi) released during the DNA polymerase reaction, the quantitative conversion of pyrophosphate to adenosine triphosphate (ATP) by sulfurylase, and the subsequent production of visible light by firefly luciferase. DNA sequences can be deduced by measuring pyrophosphate release on testing DNA/polymerase complexes with each deoxyribonucleotide triphosphate (dNTP) separately and sequentially. See Ronaghi et al., Science 281: 363 365 (1998); Hyman, Anal. Biochem. 174, 423 (1988); Harris, U.S. Pat. No. 7,767,400. Alternatively, DNA sequencing can be performed by a synthesis method mostly focused on a photocleavable chemical moiety that is linked to a fluorescent dye to cap the 3'-OH group of deoxynucleoside triphosphates (dNTPs) (Welch et al. Nucleosides and Nucleotides 18, 197 (1999) & European Journal, 5:951-960 (1999); Xu et al., U.S. Pat. No. 7,777,013; Williams et al., U.S. Pat. No. 7,645,596; Kao et al, U.S. Pat. No. 6,399,335; Nelson et al., U.S. Pat. Nos. 7,052,839 & 7,033,762; Kumar et al., U.S. Pat. No. 7,041,812; Sood et al, US Pat. App. No. 2004-0152119; Eid et al., Science 323, 133 (2009)).

Sequencing platforms are further moving away from those that read a plurality of target nucleic acids towards single molecule sequencing systems. Earlier systems analyze target nucleic acids in bulk. What this means is that, for example with Sanger sequencing, a plurality of target nucleic acids are amplified in the presence of terminating ddNTPs. Collectively, each termination position read on a gel represents a plurality of amplification products that all terminated at the same nucleobase position. Single-molecule sequencing systems can use nanostructures wherein the synthesis of a complementary strand of nucleic acid from a single template is performed. These nanostructures are typically configured to perform reads of a plurality of single strand nucleic acids. Each single strand contributes sequence information to the sequence analysis system. See, Hardin et al., U.S. Pat. No. 7,329,492; Odera, US Pub. Pat. App No. 2003-0190647. Single-molecule sequence is preferably performed in real-time, meaning that a nucleobase unit is detected before incorporation of the next nucleobase unit, as is the case for the Pacific Biosciences method mentioned above.

Sequencing technologies are known in the art. For a further review of some sequencing technologies, see Cheng, Biochem. Biophys. 22: 223 227 (1995); Mardis, Annual Review of Genomics and Human Genetics 9: 387-402 (2008) & Genome Medicine 1 (4): 40 (2009); Eid et al., Science 323, 133 (2009); Craighead et al., U.S. Pat. No. 7,316,796; Lipshutz, et al., Curr Opinion in Structural Biology., 4:376 (1994); Kapranov et al., Science 296, 916 (2002); Levene et al., U.S. Pat. No. 6,917,726, Korlach et al., U.S. Pat. No. 7,056,661; Levene et al. Science 299, 682 (2003); Flusberg et al., Nature Methods v. 7, no. 6, p. 461 (June 2010); Macevicz, U.S. Pat. Nos. 6,306,597 & 7,598,065; Balasubramanian et al., U.S. Pat. No. 7,232,656; Lapidus et al, U.S. Pat. No. 7,169,560; Rosenthal et al., U.S. Pat. No. 6,087,095; Lasken, Curr Opin Microbiol. 10(5):510 (2007); Ronaghi et al., Pharmacogenics. Volume 8, 1437-41 (2007); Keating et al., PLoS One 3(10):e3583 (2008); Pease et al., PNAS USA 91(11):5022 (1994); Lockhart, et al., Nat Biotechnol. 14(13):1675 (1996); Shendure et al., Science 309, 1728 (2005); Kim et al., Science 316, 1481 (2007); Valouev et al. Genome Research 18 (7): 1051 (2008); Cloonan et al., Nature Methods 5 (7): 613 (2008); Tang et al. Nature Methods 6 (5): 377 (2009); McKernan et al. Genome Research 19 (9): 1527 (2009); Ecker et al., Nature Reviews Microbiology 6, 553 (2008).

VI. Kits

The invention also provides kits for performing the methods for detecting target nucleic acids described herein. Preferred kits contain at least one capture probe and at least one immobilized probe as described above. Kits can also include a detection probe specific for a target nucleic acid. In preferred kits, the immobilized probe is immobilized to a magnetized particle, preferably a paramagnetic bead, with homopolymeric oligomers (e.g., polyA, polyT, polyC, or polyG) attached to it that are complementary to a homopolymeric portion of the capture probe in the kit. Kit can also include chemical compounds used in forming the capture hybrid and/or detection hybrid, such as salts, buffers, chelating agents, and other inorganic or organic compounds. Kit can also include chemical compounds used in releasing the target nucleic acid from a capture hybrid, such as salts, buffers, chelating agents, denaturants, and other inorganic or organic compounds. Kit can also include chemical compounds used in the detection step, such as enzymes, substrates, acids or bases to adjust pH of a mixture, salts, buffers, chelating agents, and other inorganic or organic compounds used in producing a detectable signal from a detection hybrid. Kit can also include chemicals for preparing samples for use in the invention methods which may include individual components or mixtures of lysing agents for disrupting tissue or cellular material and preserving the integrity of nucleic acids. Such compositions include enzymes, detergents, chaotropic agents, chelating agents, salts, buffering agents, and other inorganic or organic compounds. Kits can include any combination of the capture probe, detection probe, and immobilize probe components described above which can be packaged in combination with each other, either as a mixture or in individual containers. Kits can also contain instructions for performing the capture methods described above.

Although the invention has been described in detail for purposes of clarity of understanding, it will be obvious that certain modifications may be practiced within the scope of the appended claims. All publications and patent documents cited in this application are hereby incorporated by reference in their entirety for all purposes to the same extent as if each were so individually denoted. To the extent difference sequences might be associated with the same accession number at different times, the sequence associated with the accession number at the effective filing date is meant. The effective filing date means the earliest priority date at which the accession number at issue is disclosed. Unless otherwise apparent from the context any element, embodiment, step, feature or aspect of the invention can be performed in combination with any other

EXAMPLES

Example 1

The purpose of this experiment was to demonstrate that a homopolymer of 14 units L-thymine deoxyribose (T14) hybridizes only to an L-adenine deoxyribose polymer (A30) not to the natural (D) adenine deoxyribose polymer (A30). Magnetic particles were prepared with covalently attached immobilized probes comprising 5'-TTTTTTTTTTTTTT-3' in the left handed form for one set and in the right handed form for another set. Left and right handed chimeric capture probed having the sequence 5'-CUCUUCCAAUCGU-CCGCGUGCUUAUUU AAAAAAAAAAAAAAAAAAAAAAAAAAAAAA-3' were also prepared (underlined portion of the sequence represents the nucleic acids that were made in separate sets of left-handed form or right handed form). The target was a ribosomal RNA nucleic acid and capture was determined using an AE labeled nucleic acid probe having the sequence 5'-CUCCUAUCGUUCCAUAGUCACCCT-3'.
The target ribosomal RNA has a nucleic acid of:

TTTTTTCTGAGAATTTGATCTTGGTTCAGATTGAACGCTGGCGGCGTGGA

TGAGGCATGCAAGTCGAACGGAGCAATTGTTTCGGCAATTGTTTAGTGGC

GGAAGGGTTAGTAATGCATAGATAATTTGTCCTTAACTTGGGAATAACGG

TTGGAAACGGCCGCTAATACCGAATGTGGCGATATTTGGGCATCCGAGTA

ACGTTAAAGAAGGGGATCTTAGGACCTTTCGGTTAAGGGAGAGTCTATGT

GATATCAGCTAGTTGGTGGGGTAAAGGCCTACCAAGGCTATGACGTCTAGG

CGGATTGAGAGATTGGCCGCCAACACTGGGACTGAGACACTGCCCAGACT

CCTACGGGAGGCTGCAGTCGAGAATCTTTCGCAATGGACGGAAGTCTGAC

GAAGCGACGCCGCGTGTGTGATGAAGGCTCTAGGGTTGTAAAGCACTTTC

GCTTGGGAATAAGAGAAGGCGGTTAATACCCGCTGGATTTGAGCGTACCA

GGTAAAGAAGCACCGGCTAACTCCGTGCCAGCAGCTGCGGTAATACGGAG

GGTGCTAGCGTTAATCGGATTTATTGGGCGTAAAGGGCGTGTAGGCGGAA

AGGTAAGTTAGTTGTCAAAGATCGGGGCTCAACCCCGAGTCGGCATCTAA

TACTATTTTTCTAGAGGGTAGATGGAGAAAAGGGAATTTCACCTTCTTAG

CGGTGAAATGCGTAGATATGTGGAAGAACACCAGTGGCGAAGGCGCTTTT

CTAATTTATACCTGACGCTAAGGCGCGAAAGCAAGGGGAGCAAACAGGAT

TAGATACCCTGGTAGTCCTTGCCGTAAACGATGCATACTTGATGTGGATG

GTCTCAACCCCATCCGTGTCGGAGCTAACGCGTTAAGTATGCCGCCTGAG

GAGTACACTCGCAAGGGTGAAACTCAAAAGAATTGACGGGGCCCGCACA

AGCAGTGGAGCATGTGGTTTAATTCGATGCAACGCGAAGGACCTTACCTG

GGTTTGACATGTATATGACCGCGGCAGAAATGTCGTTTTCCGCAAGGACA

TATACACAGGTGCTGCATGGCTGTCGTCAGCTCGTGCCGTGAGGTGTTGG

GTTAAGTCCCGCAACGAGCGCAACCCTTATCGTTAGTTGCCAGCACTTAG

GGTGGGAACTCTAACGAGACTGCCTGGGTTAACCAGGAGGAAGGCGAGGA

TGACGTCAAGTCAGCATGGCCCTTATGCCCAGGGCGACACACGTGCTACA

ATGGCCAGTACAGAAGGTAGCAAGATCGTGAGATGGAGCAAATCCTCAAA

GCTGGCCCCAGTTCGGATTGTAGTCTGCAACTCGACTACATGAAGTCGGA

ATTGCTAGTAATGGCGTGTCAGCCATAACGCCGTGAATACGTTCCCGGGC

CTTGTACACACCGCCCGTCACATCATGGGAGTTGGTTTTACCTTAAGTCG

TTGACTCAACCCGCAAGGGAGAGAGGCGCCCAAGGTGAGGCTGATGACTA

GGATGAAGTCGTAACAAGGTAGCCCTACCGGAAGGTGGGGCTGGATCACC

TCCTTTTAAGGATAAGGAAGAAGCCTGAGAAGGTTTCTGACTAGGTTGGG

CAAGCATTTATATGTAAGAGCAAGCATTCTATTTCATTTGTGTTGTTAAG

AGTAGCGTGGTGAGGACGAGACATATAGTTTGTGATCAAGTATGTTATTG

TAAAGAAATAATCATGGTAACAAGTATATTTCACGCATAATAATAGACGT

TTAAGAGTATTTGTCTTTTAGGTGAAGTGCTTGCATGGATCTATAGAAAT

TACAGACCAAGTTAATAAGAGCTATTGGTGGATGCCTTGGCATTGACAGG

CGAAGAAGGACGCGAATACCTGCGAAAAGCTCCGGCGAGCTGGTGATAAG

CAAAGACCCGGAGGTATCCGAATGGGGAAACCCGGTAGAGTAATAGACTA

CCATTGCATGCTGAATACATAGGTATGCAGAGCGACACCTGCCGAACTGA

AACATCTTAGTAGGCAGAGGAAAAGAAATCGAAGAGATTCCCTGTGTAGC

GGCGAGCGAAAGGGGAATAGCCTAAACCGAGCTGATAAGGCTCGGGGTTG

TAGGATTGAGGATAAAGGATCAGGACTCCTAGTTGAACACATCTGGAAAG

ATGGATGATACAGGGTGATAGTCCCGTAGACGAAAGGAGAGAAAGACCGA

CCTCAACACCTGAGTAGGACTAGACACGTGAAACCTAGTCTGAATCTGGG

GAGACCACTCTCCAAGGCTAAATACTAGTCAATGACCGATAGTGAACCAG

TACTGTGAAGGAAAGGCGAAAAGAACCCTTGTTAAGGGAGTGAAATAGAA

CCTGAAACCAGTAGCTTACAAGCGGTCGGAGACCAATGGCCCGTAAGGGT

```
CAAGGTTGACGGCGTGCCTTTTGCATGATGAGCCAGGGAGTTAAGCTAAA
CGGCGAGGTTAAGGGATATACATTCCGGAGCCGGAGCGAAAGCGAGTTTT
AAAAGAGCGAAGAGTCGTTTGGTTTAGACACGAAACCAAGTGAGCTATTT
ATGACCAGGTTGAAGCATGGGTAAAACTATGTGGAGGACCGAACTAGTAC
CTGTTGAAAAGGTTTGGATGAGTTGTGAATAGGGGTGAAAGGCCAATCA
AACTTGGAGATATCTTGTTCTCTCCGAAATAACTTTAGGGTTAGCCTCGG
ATAATGAGCTTTTGGGGGTAGAGCACTGAATTCTAGCGGGGGCCTACCGG
CTTACCAACGGAAATCAAACTCCGAATACCAGAAGCGAGTCCGGGAGATA
GACAGCGGGGCTAAGCTTCGTTGTCGAGAGGGGAACAGCCCAGACCGCC
GATTAAGGTCCCTAATTTTATGCTAAGTGGGTAAGGAAGTGATGATTCGA
AGACAGTTGGAATGTTGGCTTAGAGGCAGCAATCATTTAAAGAGTGCGTA
ACAGCTCACCAATCGAGAATCATTGCGCCGATAATAAACGGGACTAAGCA
TAAAACCGACATCGCGGGTGTGTCGATAAGACACGCGGTAGGAGAGCGTA
GTATTCAGCAGAGAAGGTGTACCGGAAGGAGGGCTGGAGCGGATACTAGT
GAAGATCCATGGCATAAGTAACGATAAAGGGAGTGAAAATCTCCCTCGCC
GTAAGCCCAAGGTTTCCAGGGTCAAGCTCGTCTTCCCTGGGTTAGTCGGC
CCCTAAGTTGAGGCGTAACTGCGTAGACGATGGAGCAGCAGGTTAAATAT
TCCTGCACCACCTAAAACTATAGCGAAGGAATGACGGAGTAAGTTAAGCA
CGCGGACGATTGGAAGAGTCCGTAGAGCGATGAGAACGGTTAGTAGGCAA
ATCCGCTAACATAAGATCAGGTCGCGATCAAGGGGAATCTTCGGAGGAAC
CGATGGTGTGGAGCGAGGCTTTCAAGAAATAATTTCTAGCTGTTGATGGT
GACCGTACCAAAACCGACACAGGTGGGCGAGATGAATATTCTAAGGCGCG
CGAGATAACTTTCGTTAAGGAACTCGGCAAATTATCCCCGTAACTTCGGA
ATAAGGGGAGCCTTTTAGGGTGACTATGGAACGATAGGAGCCCCGGGGGG
CCGCAGAGAAATGGCCCAGGCGACTGTTTAGCAAAAACACAGCACTATGC
AAACCTCTAAGGGGAAGTATATGGTGTGACGCCTGCCCAATGCCAAAAGG
TTAAAGGGATATGTCAGCTGTAAAGCGAAGCATTGAACCTAAGCCCTGGT
GAATGGCCGCCGTAACTATAACGGTGCTAAGGTAGCGAAATTCCTTGTCG
GGTAAGTTCCGACCTGCACGAATGGTGTAACGATCTGGGCACTGTCTCAA
CGAAAGACTCGGTGAAATTGTAGTAGCAGTGAAGATGCTGTTTACCCGCG
AAAGGACGAAAAGACCCCGTGAACCTTTACTGTACTTTGGTATTGGTTTT
TGGTTTGTTATGTGTAGGATAGCCAGGAGACTAAGAACACTCTTCTTCAG
GAGAGTGGGAGTCAACGTTGAAATACTGGTCTTAACAAGCTGGGAATCTA
ACATTATTCCATGAATCTGGAAGATGGACATTGCCAGACGGGCAGTTTTA
CTGGGCGGTATCCTCCTAAAAAGTAACGGAGGAGCCCAAAGCTTATTTC
ATCGTGGTTGGCAATCACGAGTAGAGCGTAAAGGTATAAGATAGGTTGAC
TGCAAGACCAACAAGTCGAGCAGAGCGAAAGTCGGGCTTAGTGATCCGGC
GGTGGAAAGTGGAATCGCCGTCGCTTAACGGATAAAAGGTACTCCGGGGA
TAACAGGCTGATCGCCACCAAGAGTTCATATCGACGTGGCGGTTTGGCAC
CTCGATGTCGGCTCATCGCATCCTGGGGCTGGAGAAGGTCCCAAGGGTTT
GGCTGTTCGCCAATTAAAGCGGTACGCGAGCTGGGTTCAAAACGTCGTGA
ACAGTTTGGTCTCTATCCTTCGTGGGCGCAGGATACTTGAGAGGAGCTGT
TCCTAGTACGAGAGGACCGGAATGGACGAACCAATGGTGTATCGGTTGTT
TTGCCAAGAGCATAGCCGAGTAGCTACGTTCGGAAAGGATAAGCATTGAA
AGCATCTAAATGCCAAGCCTCCCTCAAGATAAGGTATCCCAATGAGACTC
CATGTAGACTACGTGGTTGATAGGTTGGAGGTGTAAGCACAGTAATGTGT
TCAGCTAACCAATACTAATAAGTCCAAAGACTTGGTCTTTTTATGATTGG
AAGAGCCGAAAGGCAAAGACAATAAGAAAAAGAGTAGAGAGTGCAAGTGC
GTAGAAGACAAGCTTTTAAGCGTCTATTAGTATACGTGAGAAACGATACC
AGGATTAGCTTGGTGATAATAGAGAGAGGA
```

The capture and hybridization reactions were performed as substantially described in the art (Pace2 kits (Gen-Probe Incorporated, San Diego, Calif. 92121); U.S. Pat. No. 6,110,678; WO 2006/007567 & US 2009-0286249). Briefly, the target nucleic acid and the probe were hybridized at 60° C. for 1 hour, and then combined with one of four target capture reaction mixtures. The four target capture reaction mixture set-up was as follow: Bead with L-immobilized probe+capture probe with L-second segment; Bead with D-immobilized probe+capture probe with D-second segment; Bead with L-immobilized probe+capture probe with D-second segment; and Bead with D-immobilized probe+capture probe with L-second segment. Controls were (1) beads+target:probe without capture probe, and (2) beads+capture probe without target:probe. The target capture reactions were incubated at about 60° C. for 30 minutes and then a room temperature for about 15 minutes. Capture reactions were washed twice with a wash buffer, target nucleic acids were eluted and AE reactions were determined on a luminometer. Table 1 shows the signal (RLU).

TABLE 1

| Condition | RLU |
| --- | --- |
| No capture probe | 1310 |
| No target | 256 |
| L-capture probe and L-immobilized probe | 59268 |
| D-capture probe and D-immobilized probe | 58253 |
| L-capture probe and D-immobilized probe | 1973 |
| D-capture probe and L-immobilized probe | 1184 |

An L-nucleic acid in the capture probe hybridizes to an L-nucleic acid in the immobilized probe to essentially the same extent as a D-nucleic acid in the capture probe hybridizes to a D-nucleic acid in the immobilized probe. A D-nucleic acid capture probe and an L-nucleic acid immobilized probe or vice versa give essentially only a background signal comparable to that when the capture probe is omitted altogether.

Example 2

The purpose of this experiment was to demonstrate that L-deoxy thymidine hybridizes only to L-deoxy adenosine and not to any other right handed natural nucleic acids. The reaction was prepared substantially as in example 1, but capture probe was provided at 2, 5, 10 and 20 pmoles per reaction. The target capture reaction mixture set-up was as follow: Bead with L-immobilized probe+capture probe with L-second segment (L-L); Bead with D-immobilized probe+capture probe with D-second segment (D-D); Bead with L-immobilized probe+capture probe with D-second segment (L-D); and Bead with D-immobilized probe+capture probe with L-second segment (D-L). Controls were (1) beads+target:probe without capture probe, and (2) beads+capture probe without target:probe. Results are presented in TABLE 2.

TABLE 2

|  | RLU | L-L (RLU) | D-D (RLU) | L-D (RLU) | D-L (RLU) | L-L % capture | D-D % capture | L-D % capture | D-L % capture |
|---|---|---|---|---|---|---|---|---|---|
| No Capture Probe | 807 | | | | | | | | |
| No Target | 227 | | | | | | | | |
| Supernatant | 43481 | | | | | | | | |
| Supernatant cont. | 5465 | | | | | | | | |
| 2 pmoles | | 145705 | 138889 | 697 | 1797 | 76.6 | 73 | 0.37 | 0.94 |
| 5 pmoles | | 159518 | 130179 | 439 | 1163 | 83.9 | 68.5 | 0.23 | 0.61 |
| 10 pmoles | | 162542 | 144574 | 489 | 803 | 86 | 76 | 0.25 | 0.42 |
| 20 pmoles | | 192300 | 129737 | 1020 | 1400 | 100 | 68.2 | 0.53 | 0.73 |

Again left handed nucleic acids and right handed complementary nucleic acids do not hybridize. The L-L capture resulted in about 77-100% recovery, the D-D capture resulted in about 68-76% recovery and the L-D and D-L captures were not above background.

Example 3

The purpose of this experiment was to compare the Tm of DdA:DdT vs LdA:LdT and to investigate whether LdA:DdT or DdA:LdT have any Tm at all. Each strand was first hybridized at about 50° C. for 1 hour followed by a room temperature incubation for 1 hour. The capture probes and immobilized probes were then incubated at increasing temperatures ranging from about 20° C. to about 80° C., and absorbance measurements were taken at numerous time intervals. Hybridizations were performed substantially as described in example 1. Absorbance against temperature of hybridization for L-nucleic acids with D-nucleic acids (LdA: dT or dA:LdT); L-nucleic acids with L-nucleic acids; and D-nucleic acids with D-nucleic acids (LdA and LdT and dA and dT) were determined. Hybrids formed from LdA and LdT and dA and dT have the same melting temperature of 52.1° C. LdA:dT or dA:LdT have no detectable melting point and thus no hybridization.

Example 4

HIV or HCV can be detected using commercial assays. The assay involves three main steps which take place in a single tube: sample preparation; HIV-1 and HCV RNA target amplification by Transcription-Mediated Amplification (TMA) (U.S. Pat. No. 5,399,491); and detection of the amplification products (amplicon) by a Hybridization Protection Assay (HPA) (Arnold et al., Clin Chem. 35:1588-1594 (1989).

During sample preparation, RNA is isolated from plasma specimens via the use of target capture. Plasma is treated with a detergent to solubilize the viral envelope, denature proteins and release viral genomic RNA. Capture probes having first segments complementary to conserved regions of HIV-1 or HCV and second segment including L-polyA, are hybridized to the HIV-1 or HCV RNA target, if present, in the test specimen. The hybridized target is then captured onto an immobilized probe of L-poly-T on magnetic microparticles that are separated from plasma in a magnetic field. Wash steps are utilized to remove extraneous plasma components from the reaction tube. Magnetic separation and wash steps are performed.

Target amplification occurs via a real-time R-TMA version of TMA, which is a transcription-based nucleic acid amplification method that utilizes two enzymes, MMLV reverse transcriptase and T7 RNA polymerase (see e.g., US 2007-0299254 and US 2006-0068380). The reverse transcriptase is used to generate a DNA copy (containing a promoter sequence for T7 RNA polymerase) of the target RNA sequence. T7 RNA polymerase produces multiple copies of RNA amplicon from the DNA copy template.

Example 5

Introduction

This example illustrates an HIV-1 L-ribose based target capture reagent (L-TCR) and target capture method developed for deep sequencing of the HIV-1 genome using 24 L-ribose Target Capture Oligos (TCO) three of which were also made in D-ribose form. This new reagent/method was shown to capture and amplify inactivated HIV-1 from Procleix HIV-1 Positive Control. Using an elution protocol and adding $\frac{1}{30}^{th}$ of eluate to the Reverse TMA reaction, 2000 copy/mL inactivated HIV-1 RNA was detected.

Bead Design

L-TCOs consisted of a terminal dA with the L-ribose beginning at the $29^{th}$ dA and the target sequence reverting to D-ribose for the dT3 and capture nucleotides.

Twenty-four TCO sequences were designed. All HIV-1 genome sequences from the 2007 curated alignment of the Los Alamos National Laboratory HIV Database were imported and a consensus alignment from the 1242 sequences was created. The TCOs, ranging from 17-36 nucleotides in length for the specific target region, were designed using the consensus sequence, Walking along the genome, TCOs were spaced from 100-882 nucleotides apart with an average spacing of 481 nucleotides. Table 3 shows the target capture oligomers. The polyA sequence of the target capture oligomer is shown in bold.

TABLE 3

| TCO | Sequence (5'→3') |
|---|---|
| A | UUUAAGCAGUGGGUUCCCUUTTAAAAAAAAAAAAAAAAAAAAAAAAAAAAAA |
| B | GCAGCUGCUUAUAUGCAGCAAUCUGAGGGTTTAAAAAAAAAAAAAAAAAAAAAAAAAAAA |
| C | ACUAGCUUGAAGCACCAUCCAAATTTAAAAAAAAAAAAAAAAAAAAAAAAAAAA |

TABLE 3-continued

| TCO | Sequence (5'→3') |
|---|---|
| D | UCCAGUCCCCCUUUUCUUUUAAAUUUAAAAAAAAAAAAAAAAAAAAAAAAAAAAAA |
| E | GUAGCUGAAGAGGCACAGGCUCCGUUUAAAAAAAAAAAAAAAAAAAAAAAAAAAAA |
| F | AAGCCUCCUACUAUCAUUAUUUAAAAAAAAAAAAAAAAAAAAAAAAAAAA |
| G | UUUAUAUUUAUAUAAUUCACUUCUCCAAUUGUCCUUUAAAAAAAAAAAAAAAAAAAAAAAAAAAA |
| H | GGAGGGGCAUACAUUGCUUUAAAAAAAAAAAAAAAAAAAAAAAAAAAAAA |
| I | UGAGGUAUUACAAUUUAUUAAUUUAAAAAAAAAAAAAAAAAAAAAAAAAAAA |
| J | UUCUUGUGGGUUGGGGUCUGUGGGUACACAGUUUAAAAAAAAAAAAAAAAAAAAAAAAAAAA |
| K | GCCACUGUCUUCUGCUCUUUCUUUAAAAAAAAAAAAAAAAAAAAAAAAAAAA |
| L | GUCUCCGCUUCUUCCUGCCAUAGGAUUAAAAAAAAAAAAAAAAAAAAAAAAA |
| M | GGUCUUCUGGGGCUUGUUCCAUCUAUCUUUAAAAAAAAAAAAAAAAAAAAAAAAAA |
| N | UCUUGUAUUACUACUGCCCCUUCACCUUUUUAAAAAAAAAAAAAAAAAAAAAAAAAAAAA |
| O | CCAUCUUCCCCUGCUAAUUUUAUUUAAAAAAAAAAAAAAAAAAAAAAAAAA |
| P | ACUAAUUUAUCUACUUGUUCAUUUCCUCCAAUUUAAAAAAAAAAAAAAAAAAAAAAAAAAAAA |
| Q | GCUAUUAAGUCUUUUGAUGGGUCAUAAUAUUUAAAAAAAAAAAAAAAAAAAAAAAAAA |
| R | UGGAAUAUUGCUGGUGAUCCUUUCCAUCCCUGUGGUUUAAAAAAAAAAAAAAAAAAAAAAAAAAAAAAA |
| S | CAUUCCUGGCUUUAAUUUUACUGGUACAGUUUCUUUAAAAAAAAAAAAAAAAAAAAAAAAAAAAA |
| T | UGCCAAAGAGUGAUUUGAGGGAAUUUAAAAAAAAAAAAAAAAAAAAAAAAAAA |
| U | CCCACUCCCUGACAUGCUGUCAUCAUUUCUUUUAAAAAAAAAAAAAAAAAAAAAAAAAAA |
| V | UUUAAAUCUUGUGGGGUGGCUCCUUCUGAUAAUGCUUUAAAAAAAAAAAAAAAAAAAAAAAAAAAAAA |
| AA | UCUGCUGUCCCUGUAAUAAACCCGUUUAAAAAAAAAAAAAAAAAAAAAAAAAAAA |
| BB | GCUGGAAUAACUUCUGCUUCUAUUUAAAAAAAAAAAAAAAAAAAAAAAAAAAA |

Target Protocol Development

Target capture was performed using substantially the compositions and known methods except for the use of L-nucleic acids (see e.g., U.S. Pat. No. 6,110,678, US 2007-0299254 and US 2006-0068380). Sample was mixed at a 1.25:1 ratio with TCR containing about 2 pmoles/reaction of one of the target capture oligomers in Table 3 and about 20-40 micrograms/reaction of magnetic beads with immobilized probes. Thus, the twenty-four separate reactions were prepared. The mixtures were heated at 60° C. for 20 minutes, then annealed on the bench for 15 minutes. The beads were washed on the Target Capture Station, which performs magnetic separation/wash, using an oil free wash solution followed by wash solution with 200 uL oil included. Washed beads were resuspended in 75 uL of Amplification Reagent, transferred to a 96-well plate and briefly centrifuged. The reaction plate was heated at 60° C. for about 10 to 15 minutes followed by a cool-down to 42° C. on-board a Stratagene Real-Time PCR instrument used here for performing Real-Time RNA transcription mediated amplification (RTMA).

After several minutes of equilibration at 42° C., 25 uL of enzyme reagent containing MMLV reverse transcriptase and T7 RNA Polymerase was added, and the reaction amplified and analyzed on the Stratagene analyzer.

L-Ribose TCO Evaluations

The L-ribose TCOs (L-TCO) were individually evaluated for target capture using HIV-1 Positive Control (500 copies/mL inactivated virus) as the target and using the HIV-1 Discriminatory assay for target detection. Each L-TCO was individually spiked at about 1.82 pmol/rxn into 20 ug/rxn magnetic particles and individually tested for target capture Controls included a: (1) "No-TCO" in TCR control; (2) TCO Sequence AA from TABLE 3 with D nucleic acids in the second segment and a D-nucleic acid immobilized probe linked to a magnetic bead; and (3) TCO Sequence AA from TABLE 3 with L-nucleic acids in the second segment and a L-nucleic acid immobilized probe linked to a magnetic bead.

L-TCOs A Through L

All TCOs exhibited capture as evidenced by amplification with the exception of TCO which yielded no target Ct (emergence time) or internal control Ct on initial or repeat testing (see Table 4. With the remaining target capture reactions, there was a variability among the individual target capture oligomers, some being substantially better than others. These varied results between the different target capture oligomers may be due to the weaker binding of the first segment to the target nucleic acid, interference from the internal control, competition between the target capture oligomers and the probe oligomers used or a combination thereof. To check for interference of the TCOs with internal control amplification, the TCO sequences were compared for matches to the internal control oligos and torch sequences. There were typically at most 4-5 consecutive base matches that might explain the interference with internal control amplification. Internal control will not be needed in the final L-TCR intended for PCR.

Summary: L-TCOs with reasonable Cts and ample signal were L-TCOs F, G, J, K, L. L-TCOs F, K, L came the closest to matching performance of the control R-TCO (AA).

TABLE 4

| Well | Dye | Bead | Capture Probe | Threshold | CT (dR) | S/N |
|---|---|---|---|---|---|---|
| A1 | FAM | RH Bead[1] | R-AA | 498.572 | 23.24 | 5.347 |
| A2 | FAM | RH Bead | R-No TCO | 498.572 | 23.83 | 3.772 |
| A3 | FAM | LH Bead[2] | L-AA | 498.572 | 23.32 | 4.45 |
| A4 | FAM | LH Bead | L-No TCO | 498.572 | 100 | 0.971 |
| A5 | FAM | LH Bead | A | 498.572 | 34.62 | 1.417 |
| A6 | FAM | LH Bead | B | 498.572 | 36.67 | 1.311 |
| A7 | FAM | LH Bead | C | 498.572 | 33.12 | 1.395 |
| A8 | FAM | LH Bead | D | 498.572 | 100 | 1.269 |
| B1 | FAM | RH Bead | R-AA | 498.572 | 23.15 | 4.49 |
| B2 | FAM | RH Bead | R-No TCO | 498.572 | 24.66 | 3.384 |
| B3 | FAM | LH Bead | L-AATCO | 498.572 | 22.31 | 5.752 |
| B4 | FAM | LH Bead | L-No TCO | 498.572 | 100 | 0.981 |
| B5 | FAM | LH Bead | A | 498.572 | 32.92 | 1.498 |
| B6 | FAM | LH Bead | B | 498.572 | 100 | 1.177 |
| B7 | FAM | LH Bead | C | 498.572 | 30.74 | 1.655 |
| B8 | FAM | LH Bead | D | 498.572 | 100 | 1.211 |

TABLE 4-continued

| Well | Dye | Bead | Capture Probe | Threshold | CT (dR) | S/N |
|---|---|---|---|---|---|---|
| C1 | FAM | RH Bead | R-AA | 498.572 | 24.27 | 4.136 |
| C2 | FAM | RH Bead | R-No TCO | 498.572 | 27.48 | 2.327 |
| C3 | FAM | LH Bead | L-AA | 498.572 | 24.72 | 3.582 |
| C4 | FAM | LH Bead | L-No TCO | 498.572 | 100 | 0.968 |
| C5 | FAM | LH Bead | A | 498.572 | 100 | 1.241 |
| C6 | FAM | LH Bead | B | 498.572 | 100 | 0.979 |
| C7 | FAM | LH Bead | C | 498.572 | 27.77 | 2.291 |
| C8 | FAM | LH Bead | D | 498.572 | 34.65 | 1.484 |
| D1 | FAM | LH Bead | E | 498.572 | 100 | 1.079 |
| D2 | FAM | LH Bead | F | 498.572 | 25.41 | 2.671 |
| D3 | FAM | LH Bead | G | 498.572 | 27.29 | 2.305 |
| D4 | FAM | LH Bead | H | 498.572 | 100 | 1.026 |
| D5 | FAM | LH Bead | I | 498.572 | 100 | 0.967 |
| D6 | FAM | LH Bead | J | 498.572 | 27.91 | 2.043 |
| D7 | FAM | LH Bead | K | 498.572 | 25.36 | 3.148 |
| D8 | FAM | LH Bead | L | 498.572 | 25.29 | 3.312 |
| E1 | FAM | LH Bead | E | 498.572 | 100 | 1.201 |
| E2 | FAM | LH Bead | F | 498.572 | 27.86 | 1.972 |
| E3 | FAM | LH Bead | G | 498.572 | 32.8 | 1.468 |
| E4 | FAM | LH Bead | H | 498.572 | 100 | 0.987 |
| E5 | FAM | LH Bead | I | 498.572 | 100 | 1.033 |
| E6 | FAM | LH Bead | J | 498.572 | 29.41 | 1.846 |
| E7 | FAM | LH Bead | K | 498.572 | 29.1 | 2.487 |
| E8 | FAM | LH Bead | L | 498.572 | 26.21 | 2.857 |
| F1 | FAM | LH Bead | E | 498.572 | 100 | 1.024 |
| F2 | FAM | LH Bead | F | 498.572 | 29.54 | 1.872 |
| F3 | FAM | LH Bead | G | 498.572 | 33.58 | 1.475 |
| F4 | FAM | LH Bead | H | 498.572 | 100 | 1.025 |
| F5 | FAM | LH Bead | I | 498.572 | 100 | 0.971 |
| F6 | FAM | LH Bead | J | 498.572 | 26.25 | 2.702 |
| F7 | FAM | LH Bead | K | 498.572 | 25.92 | 2.807 |
| F8 | FAM | LH Bead | L | 498.572 | 26.44 | 2.89 |
| A1 | TAMRA | RH Bead | R-AA | 749.768 | 25.89 | 6.842 |
| A2 | TAMRA | RH Bead | R-No TCO | 749.768 | 26.2 | 5.66 |
| A3 | TAMRA | LH Bead | L-AA | 749.768 | 25.19 | 8.137 |
| A4 | TAMRA | LH Bead | L-No TCO | 749.768 | 100 | 0.936 |
| A5 | TAMRA | LH Bead | A | 749.768 | 100 | 0.941 |
| A6 | TAMRA | LH Bead | B | 749.768 | 100 | 1.059 |
| A7 | TAMRA | LH Bead | C | 749.768 | 100 | 1.163 |
| A8 | TAMRA | LH Bead | D | 749.768 | 27.01 | 6.466 |
| B1 | TAMRA | RH Bead | R-AA | 749.768 | 67.16 | 6.942 |
| B2 | TAMRA | RH Bead | R-No TCO | 749.768 | 27.23 | 5.931 |
| B3 | TAMRA | LH Bead | L-AA | 749.768 | 25.46 | 7.903 |
| B4 | TAMRA | LH Bead | L-No TCO | 749.768 | 100 | 0.961 |
| B5 | TAMRA | LH Bead | A | 749.768 | 100 | 1.102 |
| B6 | TAMRA | LH Bead | B | 749.768 | 100 | 1.012 |
| B7 | TAMRA | LH Bead | C | 749.768 | 100 | 1.087 |
| B8 | TAMRA | LH Bead | D | 749.768 | 28.34 | 5.789 |
| C1 | TAMRA | RH Bead | R-AA | 749.768 | 26.5 | 6.553 |
| C2 | TAMRA | RH Bead | R-No TCO | 749.768 | 28.19 | 5.561 |
| C3 | TAMRA | LH Bead | L-TCO | 749.768 | 28.36 | 6.119 |
| C4 | TAMRA | LH Bead[1] | L-No TCO | 749.768 | 100 | 0.957 |
| C5 | TAMRA | LH Bead | A | 749.768 | 100 | 0.956 |
| C6 | TAMRA | LH Bead | B | 749.768 | 100 | 1.001 |
| C7 | TAMRA | LH Bead | C | 749.768 | 100 | 1.038 |
| C8 | TAMRA | LH Bead | D | 749.768 | 29.14 | 5.602 |
| D1 | TAMRA | LH Bead | E | 749.768 | 100 | 0.964 |
| D2 | TAMRA | LH Bead | F | 749.768 | 27.73 | 5.858 |
| D3 | TAMRA | LH Bead | G | 749.768 | 39.57 | 2.742 |
| D4 | TAMRA | LH Bead | H | 749.768 | 100 | 0.956 |
| D5 | TAMRA | LH Bead | I | 749.768 | 100 | 0.949 |
| D6 | TAMRA | LH Bead | J | 749.768 | 38.02 | 2.421 |
| D7 | TAMRA | LH Bead | K | 749.768 | 27.09 | 6.539 |
| D8 | TAMRA | LH Bead | L | 749.768 | 29.93 | 5.103 |
| E1 | TAMRA | LH Bead | E | 749.768 | 100 | 0.989 |
| E2 | TAMRA | LH Bead | F | 749.768 | 30.19 | 4.704 |
| E3 | TAMRA | LH Bead | G | 749.768 | 73 | 2.309 |
| E4 | TAMRA | LH Bead | H | 749.768 | 100 | 0.955 |
| E5 | TAMRA | LH Bead | I | 749.768 | 100 | 0.951 |
| E6 | TAMRA | LH Bead | J | 749.768 | 100 | 2.042 |
| E7 | TAMRA | LH Bead | K | 749.768 | 30.84 | 5.249 |
| E8 | TAMRA | LH Bead | L | 749.768 | 31.28 | 4.523 |
| F1 | TAMRA | LH Bead | E | 749.768 | 100 | 0.971 |
| F2 | TAMRA | LH Bead | F | 749.768 | 29.49 | 4.952 |
| F3 | TAMRA | LH Bead | G | 749.768 | 40.29 | 2.189 |
| F4 | TAMRA | LH Bead | H | 749.768 | 100 | 0.957 |
| F5 | TAMRA | LH Bead | I | 749.768 | 100 | 0.948 |
| F6 | TAMRA | LH Bead | J | 749.768 | 42.28 | 2.058 |
| F7 | TAMRA | LH Bead | K | 749.768 | 28.85 | 5.364 |
| F8 | TAMRA | LH Bead | L | 749.768 | 63.23 | 4.611 |

[1]RH bead = bead + D-nucleic acid
[2]LH bead = bead + L-nucleic acid
Threshold: number above which sample is called reactive
S/N: signal/noise L-TCOs #M-V Target capture reactions were performed substantially as described above for L_TCOs A-L. Based on FAM Ct and FAM Signal/Noise (TABLE 5), all target nucleic acids captured with L-TCOs M-V amplified well. For the No-TCO control, the D-ribose bead showed non-specific binding of HIV-1 and internal control, while the L-ribose bead did not. This observation indicates that nucleic acids having sequence portions that are substantially complementary to the D-nucleic acid immobilized probe, will hybridize thereto. Captured nucleic acids, then, comprise target nucleic acids and nucleic acids that hybridized directly to the D-nucleic acid immobilized probe.

Summary:

All L-TCOs, except for L-TCO I yielded a Ct time, indicating target binding, and were selected for use in the L-ribose based TCR. In contrast to the D-immobilized probes, the L-immobilized probes do not directly bind to target nucleic acids, reducing the possibility of inadvertently capturing an analyzing non-target sequences.

TABLE 5

| Well | Dye | Bead | TCO | Rlast/ Rfirst | Threshold (dR) | Ct (dR) |
|---|---|---|---|---|---|---|
| A1 | FAM | RH Bead | AA | 7.943 | 347.946 | 28.83 |
| A2 | FAM | RH Bead | No TCO | 7.499 | 347.946 | 30.64 |
| A3 | FAM | LH Bead | AA | 7.853 | 347.946 | 28.35 |
| A4 | FAM | LH Bead | No TCO | 0.997 | 347.946 | — |
| A5 | FAM | LH Bead | A | 3.231 | 347.946 | 34.04 |
| A6 | FAM | LH Bead | B | 0.953 | 347.946 | — |
| A7 | FAM | LH Bead | C | 3.694 | 347.946 | 32.97 |
| A8 | FAM | LH Bead | D | 3.63 | 347.946 | 32.99 |
| B1 | FAM | RH Bead | AA | 7.998 | 347.946 | 27.93 |
| B2 | FAM | RH Bead | No TCO | 6.255 | 347.946 | 30.9 |
| B3 | FAM | LH Bead | NA0138 | 7.171 | 347.946 | 29.39 |
| B4 | FAM | LH Bead | No TCO | 0.947 | 347.946 | — |
| B5 | FAM | LH Bead | A | 3.016 | 347.946 | 34.58 |
| B6 | FAM | LH Bead | B | 1.464 | 347.946 | 40 |
| B7 | FAM | LH Bead | C | 2.989 | 347.946 | 31.94 |
| B8 | FAM | LH Bead | D | 2.514 | 347.946 | 35.99 |
| C1 | FAM | RH Bead | AA | 7.939 | 347.946 | 28.86 |
| C2 | FAM | RH Bead | No TCO | 7.19 | 347.946 | 29.88 |
| C3 | FAM | LH Bead | AA | 7.389 | 347.946 | 29.26 |
| C4 | FAM | LH Bead | No TCO | 1.898 | 347.946 | 37.62 |
| C5 | FAM | LH Bead | A | 1.981 | 347.946 | 39.21 |
| C6 | FAM | LH Bead | B | 1.761 | 347.946 | 38.7 |
| C7 | FAM | LH Bead | C | 3.894 | 347.946 | 33.69 |
| C8 | FAM | LH Bead | D | 3.43 | 347.946 | 35.05 |
| D1 | FAM | LH Bead | E | 1.986 | 347.946 | 37.56 |
| D2 | FAM | LH Bead | F | 6.597 | 347.946 | 31.16 |
| D3 | FAM | LH Bead | G | 5.361 | 347.946 | 31.84 |
| D4 | FAM | LH Bead | H | 2.537 | 347.946 | 35.8 |
| D5 | FAM | LH Bead | I | 0.965 | 347.946 | — |
| D6 | FAM | LH Bead | J | 4.871 | 347.946 | 31.92 |
| D7 | FAM | LH Bead | K | 7.644 | 347.946 | 29.66 |
| D8 | FAM | LH Bead | L | 6.571 | 347.946 | 29.78 |
| E1 | FAM | LH Bead | E | 2.977 | 347.946 | 34.94 |

TABLE 5-continued

| Well | Dye | Bead | TCO | Rlast/Rfirst | Threshold (dR) | Ct (dR) |
|---|---|---|---|---|---|---|
| E2 | FAM | LH Bead | F | 5.858 | 347.946 | 31.01 |
| E3 | FAM | LH Bead | G | 3.673 | 347.946 | 33.93 |
| E4 | FAM | LH Bead | H | 1.886 | 347.946 | 37.86 |
| E5 | FAM | LH Bead | I | 0.967 | 347.946 | — |
| E6 | FAM | LH Bead | J | 6.228 | 347.946 | 31.66 |
| E7 | FAM | LH Bead | K | 7.32 | 347.946 | 29.86 |
| E8 | FAM | LH Bead | L | 6.758 | 347.946 | 29.51 |
| F1 | FAM | LH Bead | E | 1.677 | 347.946 | 38.92 |
| F2 | FAM | LH Bead | F | 6.231 | 347.946 | 31.44 |
| F3 | FAM | LH Bead | G | 4.005 | 347.946 | 33.79 |
| F4 | FAM | LH Bead | H | 0.99 | 347.946 | — |
| F5 | FAM | LH Bead | I | 0.953 | 347.946 | — |
| F6 | FAM | LH Bead | J | 5.917 | 347.946 | 31.76 |
| F7 | FAM | LH Bead | K | 7.373 | 347.946 | 30.29 |
| F8 | FAM | LH Bead | L | 6.87 | 347.946 | 31.02 |
| A1 | TAMRA | RH Bead | AA | 9.192 | 3056.499 | 36.11 |
| A2 | TAMRA | RH Bead | No TCO | 7.869 | 3056.499 | 41.38 |
| A3 | TAMRA | LH Bead | AA | 9.389 | 3056.499 | 39.46 |
| A4 | TAMRA | LH Bead | No TCO | 0.918 | 3056.499 | — |
| A5 | TAMRA | LH Bead | A | 0.912 | 3056.499 | — |
| A6 | TAMRA | LH Bead | B | 1.2 | 3056.499 | — |
| A7 | TAMRA | LH Bead | C | 1.18 | 3056.499 | — |
| A8 | TAMRA | LH Bead | D | 9.158 | 3056.499 | 39.62 |
| B1 | TAMRA | RH Bead | AA | 9.286 | 3056.499 | 38.41 |
| B2 | TAMRA | RH Bead | No TCO | 7.174 | 3056.499 | 42.55 |
| B3 | TAMRA | LH Bead | AA | 8.932 | 3056.499 | 40.79 |
| B4 | TAMRA | LH Bead | No TCO | 0.907 | 3056.499 | — |
| B5 | TAMRA | LH Bead | A | 0.916 | 3056.499 | — |
| B6 | TAMRA | LH Bead | B | 1.183 | 3056.499 | — |
| B7 | TAMRA | LH Bead | C | 1.165 | 3056.499 | — |
| B8 | TAMRA | LH Bead | D | 8.728 | 3056.499 | 40.93 |
| C1 | TAMRA | RH Bead | AA | 8.739 | 3056.499 | 39.83 |
| C2 | TAMRA | RH Bead | No TCO | 7.73 | 3056.499 | 41.78 |
| C3 | TAMRA | LH Bead | AA | 7.776 | 3056.499 | 42.15 |
| C4 | TAMRA | LH Bead | No TCO | 0.92 | 3056.499 | — |
| C5 | TAMRA | LH Bead | A | 0.917 | 3056.499 | — |
| C6 | TAMRA | LH Bead | B | 1.183 | 3056.499 | — |
| C7 | TAMRA | LH Bead | C | 1.157 | 3056.499 | — |
| C8 | TAMRA | LH Bead | D | 7.99 | 3056.499 | 42.22 |
| D1 | TAMRA | LH Bead | E | 0.958 | 3056.499 | — |
| D2 | TAMRA | LH Bead | F | 7.978 | 3056.499 | 42.45 |
| D3 | TAMRA | LH Bead | G | 3.762 | 3056.499 | 55.35 |
| D4 | TAMRA | LH Bead | H | 0.914 | 3056.499 | — |
| D5 | TAMRA | LH Bead | I | 0.934 | 3056.499 | — |
| D6 | TAMRA | LH Bead | J | 4.376 | 3056.499 | 52.04 |
| D7 | TAMRA | LH Bead | K | 8.671 | 3056.499 | 40.79 |
| D8 | TAMRA | LH Bead | L | 7.202 | 3056.499 | 44.53 |
| E1 | TAMRA | LH Bead | E | 0.963 | 3056.499 | — |
| E2 | TAMRA | LH Bead | F | 7.228 | 3056.499 | 43.95 |
| E3 | TAMRA | LH Bead | G | 3.573 | 3056.499 | 56.69 |
| E4 | TAMRA | LH Bead | H | 0.916 | 3056.499 | — |
| E5 | TAMRA | LH Bead | I | 0.904 | 3056.499 | — |
| E6 | TAMRA | LH Bead | J | 3.771 | 3056.499 | 55.28 |
| E7 | TAMRA | LH Bead | K | 8.813 | 3056.499 | 40.73 |
| E8 | TAMRA | LH Bead | L | 8.317 | 3056.499 | 42.39 |
| F1 | TAMRA | LH Bead | E | 0.958 | 3056.499 | — |
| F2 | TAMRA | LH Bead | F | 7.651 | 3056.499 | 43.14 |
| F3 | TAMRA | LH Bead | G | 3.981 | 3056.499 | 54.21 |
| F4 | TAMRA | LH Bead | H | 0.912 | 3056.499 | — |
| F5 | TAMRA | LH Bead | I | 0.919 | 3056.499 | — |
| F6 | TAMRA | LH Bead | J | 4.112 | 3056.499 | 53.54 |
| F7 | TAMRA | LH Bead | K | 8.104 | 3056.499 | 41.9 |
| F8 | TAMRA | LH Bead | L | 8.13 | 3056.499 | 43.69 |

Internal control was removed from the assay for the remainder of the studies.

Example 6

This example compares the performance of D- and L-capture probes in capturing varying copy number of an HIV target nucleic acid assessed by quantitative PCR of captured target.

a. L-TCR Preparation with 24 L-Ribose TCOs and Evaluation (+/−) Elution

An L-ribose target capture reagent (L-TCR) was prepared. The L-TCR consisted of about 20 ug/rxn beads and 0.1 pmol of each L-TCO in TABLE 3 except for TCO-I. TCOs AA and BB were also prepared as positive controls having D-nucleic acid second segments and combined with beads attached to D-nucleic acid immobilized probes.

Target was eluted from beads into 75 uL of water and compared to beads carried into the Amp reaction without an elution step.

A 2.5 uL quantity of the material eluted into water was spiked into 75 uL of Amp reagent for the RTMA assay. Only $1/30^{th}$ of the starting eluted material was assayed. Here the minimum tested with elution was 2000 copies/mL or 1000 copies/rxn. The plate setup for the evaluation of L-TCR performance with and without target elution is shown below in Table 6. The numbers within the plate represent the copies/mL of HIV present at that well position.

TABLE 6

| | 1.82 pmol each of 3 Standard RH-TCOs | | | | | | 0.1 pmol each of 24 LH-TCOs | | | | | |
|---|---|---|---|---|---|---|---|---|---|---|---|---|
| | No Elution | | | +Elution | | | No Elution | | | +Elution | | |
| | 1 | 2 | 3 | 4 | 5 | 6 | 7 | 8 | 9 | 10 | 11 | 12 |
| A | 0 | 0 | 0 | 0 | 0 | 0 | 0 | 0 | 0 | 0 | 0 | 0 |
| B | 30 | 30 | 30 | 1k | 1k | 1k | 1k | 1k | 1k | 1k | 1k | 1k |
| C | 100 | 100 | 100 | 3k | 3k | 3k | 3k | 3k | 3k | 3k | 3k | 3k |
| D | 300 | 300 | 300 | 10k | 10k | 10k | 10k | 10k | 10k | 10k | 10k | 10k |
| E | 1k | 1k | 1k | 30k | 30k | 30k | 30k | 30k | 30k | 30k | 30k | 30k |
| F | 3k | 3k | 3k | — | — | — | — | — | — | — | — | — |
| G | 10k | 10k | 10k | — | — | — | — | — | — | — | — | — |
| H | — | — | — | — | — | — | — | — | — | — | — | — |

Following target capture, real-time RTMA was performed as generally described above, and the results are present in Tables 7 and 8. Ct Times are shown in Table 7.

Figure 2:
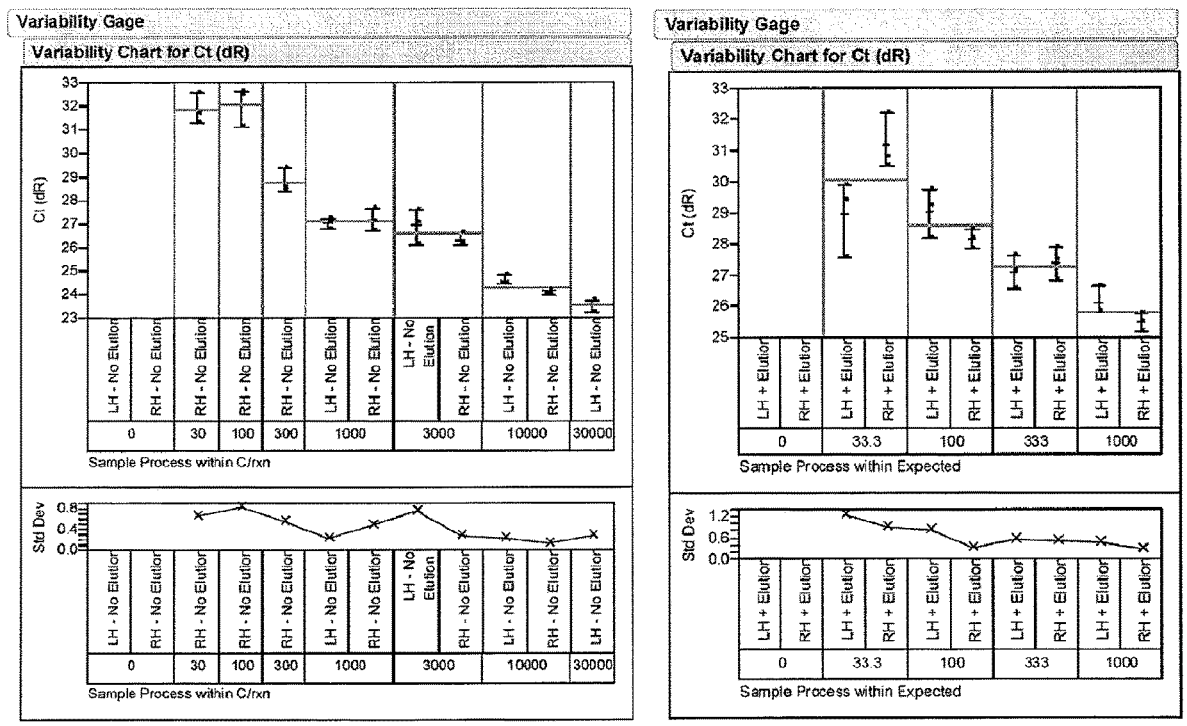
FIG. 2 compares quantitative PCR emergence times for targets captured with different capture probes.

Table 8 shows Ct Emergence times comparing D-TCR (RH) and L-TCR (LH) with and without elution of target at several target concentrations. The starting copy number for the (+) elution data is $\frac{1}{30}^{th}$ of the total eluted material i.e. copies present at the start of RTMA. FIG. 2 shows the same data shown in Table 8. FIG. 2 shows L-TCR plotted next to D-TCR for comparison of CT emergence times. The data shown in FIG. 2 are broken out into (−) Elution (beads carried into reaction) and (+) Elution ($\frac{1}{30}^{th}$ sample into reaction).

For "No-Elution", L-TCR performance based on Ct was similar to D-TCR at 1000 and 3000 c/rxn. At 10,000 c/rxn, D-TCR was slightly faster. For the eluted samples, L-TCR performance based on Ct was similar to D-TCR at 100 and 333 c/rxn. L-TCR was faster at 33 c/rxn and D-TCR was faster at 1000 c/rxn. The L-ribose based TCR successfully detected 2000 copies/mL using only a 2.5 uL volume (50 copies) of HIV-1 inactivated virus.

TABLE 7

| Well | Well Name | Dye | Assay | Threshold (dR) | Ct (dR) | Quantity (copies) before amp. |
|---|---|---|---|---|---|---|
| A1 | — | FAM | FAM | 5331.279 | No Ct | No Ct |
| A2 | — | FAM | FAM | 5331.279 | No Ct | No Ct |
| A3 | — | FAM | FAM | 5331.279 | No Ct | No Ct |
| A4 | RH + Elution - 0 | FAM | FAM | 5331.279 | No Ct | No Ct |
| A5 | RH + Elution - 0 | FAM | FAM | 5331.279 | No Ct | No Ct |
| A6 | RH + Elution - 0 | FAM | FAM | 5331.279 | No Ct | No Ct |
| A7 | LH − No Elution - 0 | FAM | FAM | 5331.279 | No Ct | No Ct |
| A8 | LH − No Elution - 0 | FAM | FAM | 5331.279 | No Ct | No Ct |
| A9 | LH − No Elution - 0 | FAM | FAM | 5331.279 | No Ct | No Ct |
| A10 | LH + Elution - 0 | FAM | FAM | 5331.279 | No Ct | No Ct |
| A11 | LH + Elution - 0 | FAM | FAM | 5331.279 | No Ct | No Ct |
| A12 | LH + Elution - 0 | FAM | FAM | 5331.279 | No Ct | No Ct |
| B1 | 30 | FAM | FAM | 5331.279 | 34.3 | 1.22E+02 |
| B2 | 30 | FAM | FAM | 5331.279 | 34.58 | 1.05E+02 |
| B3 | 30 | FAM | FAM | 5331.279 | 35.88 | 5.17E+01 |
| B4 | RH + Elution - 1k | FAM | FAM | 5331.279 | 33.36 | 2.04E+02 |
| B5 | RH + Elution - 1k | FAM | FAM | 5331.279 | 32.95 | 2.54E+02 |
| B6 | RH + Elution - 1k | FAM | FAM | 5331.279 | 37 | 2.82E+01 |
| B7 | LH − No Elution - 1k | FAM | FAM | 5331.279 | 29.34 | 1.80E+03 |
| B8 | LH − No Elution - 1k | FAM | FAM | 5331.279 | 29.71 | 1.48E+03 |
| B9 | LH − No Elution - 1k | FAM | FAM | 5331.279 | 29.77 | 1.43E+03 |
| B10 | LH + Elution - 1k | FAM | FAM | 5331.279 | 31.92 | 4.46E+02 |
| B11 | LH + Elution - 1k | FAM | FAM | 5331.279 | 32.34 | 3.54E+02 |
| B12 | LH + Elution - 1k | FAM | FAM | 5331.279 | 29.97 | 1.29E+03 |
| C1 | — | FAM | FAM | 5331.279 | 33.88 | 1.00E+02 |
| C2 | — | FAM | FAM | 5331.279 | 35.48 | 1.00E+02 |
| C3 | — | FAM | FAM | 5331.279 | 35.7 | 1.00E+02 |
| C4 | RH + Elution - 3k | FAM | FAM | 5331.279 | 30.87 | 7.87E+02 |
| C5 | RH + Elution - 3k | FAM | FAM | 5331.279 | 31.07 | 7.04E+02 |
| C6 | RH + Elution - 3k | FAM | FAM | 5331.279 | 30.35 | 1.04E+03 |
| C7 | LH − No Elution - 3k | FAM | FAM | 5331.279 | 30.37 | 1.03E+03 |
| C8 | LH − No Elution - 3k | FAM | FAM | 5331.279 | 29.86 | 1.36E+03 |
| C9 | LH − No Elution - 3k | FAM | FAM | 5331.279 | 28.67 | 2.60E+03 |
| C10 | LH + Elution - 3k | FAM | FAM | 5331.279 | 31.74 | 4.91E+02 |
| C11 | LH + Elution - 3k | FAM | FAM | 5331.279 | 32.12 | 3.98E+02 |
| C12 | LH + Elution - 3k | FAM | FAM | 5331.279 | 30.5 | 9.62E+02 |
| D1 | 300 | FAM | FAM | 5331.279 | 31.21 | 6.54E+02 |
| D2 | 300 | FAM | FAM | 5331.279 | 31.04 | 7.16E+02 |
| D3 | 300 | FAM | FAM | 5331.279 | 32.08 | 4.09E+02 |
| D4 | RH + Elution - 10k | FAM | FAM | 5331.279 | 30.32 | 1.06E+03 |
| D5 | RH + Elution - 10k | FAM | FAM | 5331.279 | 30.07 | 1.21E+03 |
| D6 | RH + Elution - 10k | FAM | FAM | 5331.279 | 29.44 | 1.71E+03 |
| D7 | LH − No Elution - 10k | FAM | FAM | 5331.279 | 26.94 | 6.64E+03 |
| D8 | LH − No Elution - 10k | FAM | FAM | 5331.279 | 26.87 | 6.88E+03 |
| D9 | LH − No Elution - 10k | FAM | FAM | 5331.279 | 27.4 | 5.18E+03 |
| D10 | LH + Elution - 10k | FAM | FAM | 5331.279 | 30.18 | 1.14E+03 |
| D11 | LH + Elution - 10k | FAM | FAM | 5331.279 | 29.72 | 1.47E+03 |
| D12 | LH + Elution - 10k | FAM | FAM | 5331.279 | 29.1 | 2.06E+03 |
| E1 | — | FAM | FAM | 5331.279 | 29.22 | 1.00E+03 |
| E2 | — | FAM | FAM | 5331.279 | 29.67 | 1.00E+03 |
| E3 | — | FAM | FAM | 5331.279 | 30.27 | 1.00E+03 |
| E4 | RH + Elution - 30k | FAM | FAM | 5331.279 | 28.06 | 3.61E+03 |
| E5 | RH + Elution - 30k | FAM | FAM | 5331.279 | 27.76 | 4.26E+03 |
| E6 | RH + Elution - 30k | FAM | FAM | 5331.279 | 28.24 | 3.28E+03 |
| E7 | LH − No Elution - 30k | FAM | FAM | 5331.279 | 26.36 | 9.12E+03 |
| E8 | LH − No Elution - 30k | FAM | FAM | 5331.279 | 25.88 | 1.18E+04 |
| E9 | LH − No Elution - 30k | FAM | FAM | 5331.279 | 26.24 | 9.68E+03 |
| E10 | LH + Elution - 30k | FAM | FAM | 5331.279 | 29.16 | 1.99E+03 |
| E11 | LH + Elution - 30k | FAM | FAM | 5331.279 | 28.42 | 2.97E+03 |
| E12 | LH + Elution - | FAM | FAM | 5331.279 | 28.4 | 3.01E+03 |

TABLE 7-continued

| Well | Well Name | Dye | Assay | Threshold (dR) | Ct (dR) | Quantity (copies) before amp. |
|---|---|---|---|---|---|---|
| F1 | 30k 3000 | FAM | FAM | 5331.279 | 28.72 | 2.53E+03 |
| F2 | 3000 | FAM | FAM | 5331.279 | 28.83 | 2.39E+03 |
| F3 | 3000 | FAM | FAM | 5331.279 | 29.18 | 1.97E+03 |
| F4 | — | FAM | FAM | 5331.279 | No Ct | No Ct |
| F5 | — | FAM | FAM | 5331.279 | No Ct | No Ct |
| F6 | — | FAM | FAM | 5331.279 | No Ct | No Ct |
| F7 | — | FAM | FAM | 5331.279 | No Ct | No Ct |
| F8 | — | FAM | FAM | 5331.279 | No Ct | No Ct |
| F9 | — | FAM | FAM | 5331.279 | No Ct | No Ct |
| F10 | — | FAM | FAM | 5331.279 | No Ct | No Ct |
| F11 | — | FAM | FAM | 5331.279 | No Ct | No Ct |
| F12 | — | FAM | FAM | 5331.279 | No Ct | No Ct |
| G1 | — | FAM | FAM | 5331.279 | 26.66 | 1.00E+04 |
| G2 | — | FAM | FAM | 5331.279 | 26.46 | 1.00E+04 |
| G3 | — | FAM | FAM | 5331.279 | 26.49 | 1.00E+04 |
| G4 | — | FAM | FAM | 5331.279 | No Ct | No Ct |
| G5 | — | FAM | FAM | 5331.279 | No Ct | No Ct |
| G6 | — | FAM | FAM | 5331.279 | No Ct | No Ct |
| G7 | — | FAM | FAM | 5331.279 | No Ct | No Ct |
| G8 | — | FAM | FAM | 5331.279 | No Ct | No Ct |
| G9 | — | FAM | FAM | 5331.279 | No Ct | No Ct |
| G10 | — | FAM | FAM | 5331.279 | No Ct | No Ct |
| G11 | — | FAM | FAM | 5331.279 | No Ct | No Ct |
| G12 | — | FAM | FAM | 5331.279 | No Ct | No Ct |
| H1 | — | FAM | FAM | 5331.279 | No Ct | No Ct |
| H2 | — | FAM | FAM | 5331.279 | No Ct | No Ct |
| H3 | — | FAM | FAM | 5331.279 | No Ct | No Ct |
| H4 | — | FAM | FAM | 5331.279 | No Ct | No Ct |
| H5 | — | FAM | FAM | 5331.279 | No Ct | No Ct |
| H6 | — | FAM | FAM | 5331.279 | No Ct | No Ct |
| H7 | — | FAM | FAM | 5331.279 | No Ct | No Ct |
| H8 | — | FAM | FAM | 5331.279 | No Ct | No Ct |
| H9 | — | FAM | FAM | 5331.279 | No Ct | No Ct |
| H10 | — | FAM | FAM | 5331.279 | No Ct | No Ct |
| H11 | — | FAM | FAM | 5331.279 | No Ct | No Ct |
| H12 | — | FAM | FAM | 5331.279 | No Ct | No Ct |

TABLE 8

| Sample Copies/ 500 uL | Control Condition: 1.82 pmol each of 3 Standard RH-TCOs/20 ug beads/rxn Ct Emergence time | | Test Condition: 0.1 pmol each of 24 LH-TCOs/20 ug beads/rxn Ct Emergence time | |
|---|---|---|---|---|
| | No Elution | +Elution | No Elution | +Elution |
| 0 | No Ct | No Ct | No Ct | No Ct |
| 0 | No Ct | No Ct | No Ct | No Ct |
| 0 | No Ct | No Ct | No Ct | No Ct |
| 1000 | 26.72 | 30.77 | 26.79 | 29.41 |
| 1000 | 27.09 | 30.53 | 27.12 | 29.9 |
| 1000 | 27.66 | 32.21 | 27.21 | 27.57 |
| 3000 | 26.11 | 28.2 | 27.6 | 29.24 |
| 3000 | 26.17 | 28.46 | 27.07 | 29.77 |
| 3000 | 26.63 | 27.85 | 26.11 | 28.18 |
| 10000 | 24.17 | 27.87 | 24.45 | 27.64 |
| 10000 | 23.94 | 27.47 | 24.43 | 27.14 |
| 10000 | 23.99 | 26.84 | 24.81 | 26.54 |
| 30000 | | 25.47 | 23.74 | 26.63 |
| 30000 | | 25.19 | 23.25 | 25.86 |
| 30000 | | 25.75 | 23.72 | 25.81 |
| 30 | 31.29 | | | |
| 30 | 31.66 | | | |
| 30 | 32.55 | | | |
| 100 | 31.11 | | | |
| 100 | 32.42 | | | |
| 100 | 32.62 | | | |
| 300 | 28.55 | | | |
| 300 | 28.41 | | | |
| 300 | 29.41 | | | |

Example 7

A plasma sample from a human infected with HIV is subject to parallel processing and sequence analysis to compare L- and D-capture probes and complementary L- and D-immobilized probes. The immobilized probes include homopolymers of thymine L-deoxyribose and thymine D-deoxyribose (L- and D-polyT) respectively. The capture probes include homopolymers of adenine L-deoxyribose and adenine D-deoxyribose (L- and D-polyA) respectively. Plasma is treated with detergent to solubilize the viral envelope, denature proteins and release viral genomic RNA. Both capture probes including a target-binding segment specific for a conserved region of an HIV genomic RNA target. Parallel samples are contacted with capture and immobilized probes under the conditions as described in Example 5 or as generally described in this application. In both samples being processed, target HIV genomic RNA binds to the capture probe which binds to the immobilized probe. However, in the sample treated with the D-capture probe and D-immobilized probe, poly-A mRNA in the sample unrelated to the HIV genomic RNA target, binds directly to the immobilized probe by D-polyA binding to D-polyT. No such binding occurs in the sample receiving L-capture probe and L-immobilized probe.

The captured nucleic acids are subjected to amplification (e.g., RT-PCR or RTMA) using primers specific for the intended HIV genomic RNA target. The amplification enriches for the intended target relative to unrelated contaminant nucleic acids that directly bound the D-immobilized probe. However, significant amounts of contaminant nucleic acids are still present after the amplification from the nucleic acids captured by the D-immobilized probe but not from the amplification product captured by the L-immobilized probe.

The nucleic acids resulting from amplification are then ligated to SMRT-Bell™ adapters and subjected to single-molecule real-time sequencing (Korlach et al., *Nucleosides, Nucleotides and Nucleic Acids,* 27:1072-1083 (2008), U.S. Pat. Nos. 7,181,122, 7,302,146, and 7,313,308). In such a format, circular templates are sequenced individually and an incorporated nucleobase unit is detected in real time before incorporation of the next incorporated nucleobase unit. Sequencing of an individual templates can take place in a cylindrical metallic chamber known as a zero mode waive guide, and many such individual templates each in its own zero mode waive guide can be sequenced in parallel.

The sequences identified from the sample treated with L-nucleotide probes are substantially all the intended HIV target nucleic acid. Individual sequencing reads may differ from one another due to the sample containing a mixed population of sequence variants and because of sequencing errors. Individual sequence reads are compiled to determine the sequences of individual viral variants present in the population including a majority species and minority species represented at lower frequency. The existence of minority species may provide an indication of emerging drug resistances. The sequences identified from the sample treated with D-nucleotide probes also include such sequences of the intended target subject to similar variation due to viral variants and sequencing errors. However, sequences from non-target polyA mRNA are also present in the sample. The presence of such spurious sequences complicates analysis, for example, in distinguishing genuine variation between HIV sequences and sequencing errors.

What is claimed is:

1. A method of capturing a target nucleic acid, comprising:
contacting a target nucleic acid in a sample with a capture probe and an immobilized probe, the capture probe comprising a first segment that binds to the target nucleic acid and a second segment that binds to the immobilized probe, wherein the second segment of the capture probe and the immobilized probe comprise L-nucleic acids that can hybridize to one another, wherein the second segment of the capture probe and the immobilized probe comprise complementary homopolymeric L-nucleic acids that can hybridize to one another, wherein the homopolymeric L-nucleic acids are polyA and polyT, wherein the target nucleic acid binds to the first segment of the capture probe, and the second segment of the capture probe binds to the immobilized probe, thereby capturing the target nucleic acid, wherein the target nucleic acid is amplified before or after capture, and the method further comprises sequencing the target nucleic acid, wherein the sample comprises mRNA or nucleic acids derived therefrom, wherein the copy number of the target nucleic acid in the sample is up to 33 copies before amplification.

2. The method of claim 1, wherein the first segment includes a D nucleic acid of at least 10 D-nucleobase units complementary to the target nucleic acid.

3. The method of claim 1, wherein the first segment includes a D-nucleic acid of 10-30 D-nucleobase units complementary to the target nucleic acid.

4. The method of claim 1, wherein the first segment binds non-specifically to the target nucleic acid.

5. The method of claim 4, wherein the first segment includes a random sequence of D-nucleobase units that binds nonspecifically to the target nucleic acid.

6. The method of claim 1, wherein the second segment includes an L-nucleic acid of at least six L-nucleobase units complementary to an L-nucleic acid of at least six L-nucleobase units in the immobilized probe.

7. The method of claim 1, wherein the second segment includes an L-nucleic acid of 10-30 L-nucleobase units complementary to an L-nucleic acid of 10-30 contiguous L-nucleobase units in the immobilized probe.

8. The method of claim 7, wherein the L-nucleic acid of the second segment is a homopolymer and the L-nucleic acid of the immobilized probe constitutes a complementary homopolymer.

9. The method of claim 7, when the homopolymer of the second segment is a homopolymer of adenine nucleobase units and the homopolymer of the immobilized probed is a homopolymer of thymine nucleobase units or vice versa.

10. The method of claim 1, wherein the target nucleic acid is contacted with the capture probe and immobilized probe simultaneously.

11. The method of claim 1, wherein the binding of the target nucleic acid to the capture probe occurs under first hybridization conditions and the binding of the capture probe to the immobilized probe occurs under second hybridization conditions.

12. The method of claim 11, wherein the first conditions are more stringent than the second conditions.

13. The method of claim 1, wherein the binding of the target nucleic acid to the capture probe and the binding of the capture probe to the immobilized probe occur under the same hybridization conditions.

14. The method of claim 1, wherein the immobilized probe is immobilized to a magnetic bead.

15. The method of claim 1, wherein the target nucleic acid is provide as a component of a sample and the method further comprising separating the captured target nucleic acid from other components of the sample.

16. The method of claim 15, further comprising dissociating the captured target nucleic acid from the immobilized probe.

17. The method of claim 1, further comprising amplifying the target nucleic acid, wherein the amplifying is performed after dissociating the target nucleic acid from the capture probe.

18. The method of claim 1, wherein the target nucleic acid is an HIV nucleic acid.

19. The method of claim 1, wherein the sequencing is single molecule real time sequencing.

* * * * *